US009708653B2

(12) United States Patent
Regensburger et al.

(10) Patent No.: US 9,708,653 B2
(45) Date of Patent: Jul. 18, 2017

(54) METHODS AND COMPOSITIONS FOR IDENTIFYING REPEATING SEQUENCES IN NUCLEIC ACIDS

(71) Applicant: BATTELLE MEMORIAL INSTITUTE, Columbus, OH (US)

(72) Inventors: Joseph J. Regensburger, Grove City, OH (US); Aaron J. Sander, North Lewisburg, OH (US); Jared M. Schuetter, Columbus, OH (US); Daniel M. Bornman, Powell, OH (US); Seth A. Faith, Dublin, OH (US); Scott C. Nelson, Columbus, OH (US); Brian A. Young, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 225 days.

(21) Appl. No.: 14/379,128

(22) PCT Filed: Feb. 15, 2013

(86) PCT No.: PCT/US2013/026346
§ 371 (c)(1),
(2) Date: Aug. 15, 2014

(87) PCT Pub. No.: WO2013/123330
PCT Pub. Date: Aug. 22, 2013

(65) Prior Publication Data
US 2015/0051083 A1 Feb. 19, 2015

Related U.S. Application Data

(60) Provisional application No. 61/599,352, filed on Feb. 15, 2012.

(51) Int. Cl.
*G01N 33/48* (2006.01)
*G01N 33/50* (2006.01)
*C12Q 1/68* (2006.01)
*G06F 19/24* (2011.01)
*G06F 19/22* (2011.01)

(52) U.S. Cl.
CPC ......... *C12Q 1/6869* (2013.01); *C12Q 1/6809* (2013.01); *G06F 19/22* (2013.01); *G06F 19/24* (2013.01)

(58) Field of Classification Search
None
See application file for complete search history.

(56) References Cited

U.S. PATENT DOCUMENTS

2012/0122093 A1* 5/2012 Hennessy ............ C12Q 1/6827
435/6.11

OTHER PUBLICATIONS

Li et al. A wavelet packet based approach for the research of the avian influenza virus cross-species infection. 2010 First International Conference on Networking and Distributed Computing, pp. 301-304.*
PCT Search Report and Written Opinion for PCT/US2013/026346, completed Jul. 17, 2013.
Mansfield, E. S., et al., "Analysis of Multiplexed Short Tandem Repeat (STR) Systems Using Capillary Array Electrophoresis", 1998, Electrophoresis, vol. 19, Nr: 1, pp. 101-107.
Wang, Wei, et al., "Computing Linear Transforms of Symbolic Signals", 2002, IEEE Transactions on Signal Processing, vol. 50, Nr: 3, pp. 628-634.
Jiang, Rong, et al., "Detection and 2-Dimensional Display of Short Tandem Repeats Based on Signal, Decomposition", 2011, Int. J. Data Mining and Bioinformatics, vol. 5, No. 6, pp. 661-690.
Crowther, Greg, "Sequencing Hones in on Targets", 2012, Genetic Engineering & Biotechnology News, vol. 32, No. 18.
Tsonis, A. A., et al., "Wavelet Analysis of DNA Sequences", 1996, The American Physical Society, Physical Review E, vol. 53, No. 2, pp. 1828-1838.
Ning, Jianchang, et al., "Preliminary Wavelet Analysis of Genomic Sequences", Bioinformatics Conference, Proceedings of the 2003 IEEE Aug. 11-14, 2003, pp. 509-510.
Myers, S., et al., "The Distribution and Causes of Meiotic Recombination in the Human Genome", 2006, Biochemical Society Transactions, vol. 34, Part 4, pp. 526-530.
Murray, Kevin B., et al., "Wavelet Transforms for the Characterization and Detection of Repeating Motifs", 2002, J. Mol. Biol., vol. 316, pp. 341-363.

* cited by examiner

*Primary Examiner* — Russell S Negin
(74) *Attorney, Agent, or Firm* — Barnes & Thornburg LLP

(57) ABSTRACT

Short Tandem Repeats are currently used by law enforcement and others, for example, for the identification of individuals by DNA matching. A method is described herein that uses WPD to classify and identify repeating sequences in nucleotide sequences from the position and frequency information contained within nucleotide sequences. This decomposition allows for the quick classification of nucleotide sequences (i.e., reads) into two different classes, including, for example, one class that contains sequencer reads that contain a repeat motif with non-repeat sequence on either flank, and another class that contains sequencer reads that do not contain any repeat sequence.

20 Claims, 15 Drawing Sheets

| BEST FITTING VARIANTS FOR EACH STR TYPE | STARTING INDEX OF BEST FIT | % PATTERN MATCHED |
|---|---|---|
| CSF1PO_15 | 12 | 0.5923 |
| D13S317_15 | 3 | 0.5692 |
| D16S539_12 | 10 | 0.4000 |
| D21S11_34.2 | -11 | 0.6231 |
| D3S1358_19 | 13 | 0.5846 |
| D5S818_16 | 3 | 0.6077 |
| D7S820_14 | 16 | 0.5692 |
| D8S1179_13 | 3 | 0.9923 |

METHODS AND COMPOSITIONS FOR IDENTIFYING REPEATING SEQUENCES IN NUCLEIC ACIDS

CROSS-REFERENCE TO RELATED APPLICATIONS

This application is a U.S. national application under 35 U.S.C. §371(b) of International Application Serial No. PCT/US2013/026346 filed Feb. 15, 2013, and claims priority under 35 U.S.C. §119(e) to U.S. Provisional Application Ser. No. 61/599,352 filed Feb. 15, 2012, which is expressly incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 12, 2014, is named 920006-224202 SL.txt and is 18,462 bytes in size.

TECHNICAL FIELD

This invention relates to methods and compositions for identifying repeating sequences in nucleic acids. More particularly, the invention relates to methods and compositions for identifying repeating sequences such as tandem repeats, including microsatellites or minisatellites, in nucleic acids.

BACKGROUND

Tandem repeats of nucleotide sequences are found throughout the human genome and are sufficiently unique to an individual that these repeating sequences can be used in human or other organism identification. These markers are also useful in genetic mapping and linkage analysis. The sequences are important for determining, for example, predisposition for disease, disease diagnosis, and human identity, such as in forensics analysis. There are many types of tandem repeats of nucleic acids, including variable number tandem repeats (e.g., minisatellites and microsatellites). Microsatellites include short tandem repeats (STRs).

One application of tandem repeat analysis is in forensics or human identity testing. In current forensics analyses, highly polymorphic STRs are identified using a DNA sample from an individual and DNA amplification steps, such as polymerase chain reaction, to provide amplified samples of partial DNA sequences, or amplicons, from the individual's DNA. The amplicons can then be matched by size (i.e. repeat numbers) to reference databases, such as the sequences stored in national or local DNA databases. For example, amplicons that originate from STR loci can be matched to reference STR databases, including the FBI CODIS database in the United States, or the NDNAD database in Europe, to identify the individual by matching to the STR alleles specific to that individual.

SUMMARY OF THE INVENTION

Sequencing, including massively parallel sequencing, is an alternate method by which nucleic acid STRs can be found. Rapid methods are needed of identifying which sequencer reads contain tandem repeats to allow for quicker human identity testing, disease diagnosis, biological warfare agent identification, and for other purposes. The present inventors have discovered a method that uses wavelet packet decomposition (WPD) to classify and identify tandem repeats (e.g., STRs) in nucleic acid sequences. The WPD method allows for the quick classification of sequence data "reads" into two different classes. One class contains sequencer reads that have a repeat motif with non-repeat sequence on either flank. The other class contains sequencer reads that do not have any repeat sequence.

Wavelets are mathematical objects that can be used to find local, periodic patterns within a larger signal. Tandem repeats in nucleic acids have an inherent periodicity. As such, WPD can be used to detect these periodic signals within a nucleic acid sequence. Tandem repeats, and other periodic patterns, are identified by the method described herein by characteristic patterns in the wavelet packet basis, and non-periodic data are classified. The method greatly reduces the amount of data that needs to be analyzed using traditional alignment software, leading to shorter alignment times, and less sensitivity to misreads. Thus, the method provides a novel approach using WPD to identify both the length and frequency of tandem repeats in nucleic acid sequences. This provides quicker and more accurate human identity testing and disease diagnosis, for example, than can be achieved with presently used methods.

In one illustrative embodiment of the invention, a method for identifying repeating sequences in a target nucleic acid comprising repeating sequences and non-repeating sequences is provided. The method comprises the steps of i) sequencing the target nucleic acid to obtain sequence data wherein the sequence data is digitized and the digitized sequence data is decomposed using WPD, wherein the WPD generates data comprising non-periodic signal data and periodic signal data comprising coefficients, wherein the non-periodic signal data is classified into a non-repeat bin, and wherein the periodic signal data is placed in a repeat bin; and ii) identifying the repeating sequences in the target nucleic acid by matching the coefficients from the periodic signal data in the repeat bin to coefficients generated from WPD of a reference sequence.

In yet another embodiment, coefficients from both the WPD of the sequence data and the WPD of the reference sequence can be computed. In another embodiment, the coefficients from the WPD of the sequence data can be matched via an alignment, for example, or another method, to a subset of coefficients from the WPD of the reference sequence, corresponding to a repeat type. In this manner, the WPD coefficients can be used to identify the type of repeat pattern present in the target nucleic acid. In another embodiment, WPD can be used instead of an alignment algorithm to match the coefficients from the WPD of the sequence data to a subset of coefficients from the WPD of the reference sequence.

In various embodiments, the method described herein provides information selected from the group consisting of the location, the frequency, and the length of the repeating sequences, or a combination thereof, in the target nucleic acid. In another aspect, the repeat type identified is compared to data in a nucleic acids database, such as a DNA database (e.g., CODIS or NDNAD).

Any of the embodiments of the invention described in the following numbered clauses are also contemplated and are within the scope of the invention—

1. A method for identifying repeating sequences in a target nucleic acid comprising repeating sequences and non-repeating sequences, the method comprising the steps of i) sequencing the target nucleic acid to obtain sequence data wherein the sequence data is digitized and the digitized sequence data is decomposed using WPD, wherein the WPD generates data comprising non-periodic signal data and periodic signal data comprising coefficients, wherein the non-periodic signal data is classified into a non-repeat bin, and wherein the periodic signal data is placed in a repeat bin; and ii) identifying the repeating sequences in the target nucleic acid by matching the coefficients from the periodic signal data in the repeat bin to coefficients generated from WPD of a reference sequence.

2. The method of clause 1 wherein the repeating sequences comprise different loci.

3. The method of clause 2 wherein the different repeating sequence loci have distinguishable coefficients and the distinguishable coefficients allow the different repeating sequence loci to be distinguished from each other.

4. The method of any one of clauses 1 to 3 wherein the target nucleic acid comprises more than one allele for each of the loci containing repeating sequences in the target nucleic acid.

5. The method of clause 4 wherein the different alleles have distinguishable coefficients and wherein the distinguishable coefficients allow the different alleles to be distinguished from each other.

6. The method of any one of clauses 1 to 5 wherein the matching step comprises the step of using an allele calling algorithm including allele calling by an alignment algorithm or other similarity search.

7. The method of any one of clauses 1 to 5 wherein the matching step comprises the step of using WPD.

8. The method of any one of clauses 1 to 7 wherein the method provides information selected from the group consisting of the location, the frequency, and the length of the repeating sequences, or a combination thereof, in the target nucleic acid.

9. The method of any one of clauses 1 to 8 wherein one or more repeating sequences identified are compared to sequence data in a DNA database.

10. The method of clause 9 wherein the database is a national government DNA database.

11. The method of clause 9 or 10 wherein the database is selected from the group consisting of CODIS, NDNAD, and FNAEG.

12. The method of any one of clauses 9 to 11 wherein the database is CODIS.

13. The method of any one of clauses 9 to 11 wherein the database is NDNAD.

14. The method of clause 9 wherein the database is GenBank.

15. The method of any one of clauses 9 to 13 wherein the repeating sequences are STRs and the sequence data in the DNA database comprises STR loci.

16. The method of any one of clauses 9 to 13 or 15 wherein the repeating sequences are STRs and the sequence data in the DNA database comprises about 7 to about 16 STR loci.

17. The method of any one of clauses 1 to 16 wherein the reference sequence contains STRs.

18. The method of clause 17 wherein the reference sequence further comprises an allele for each STR.

19. The method of any one of clauses 1 to 18 wherein the target nucleic acid is a DNA or an RNA.

20. The method of any one of clauses 1 to 19 wherein the repeating sequences are tandem repeats.

21. The method of clause 20 wherein the tandem repeats are variable number tandem repeats.

22. The method of clause 21 wherein the variable number tandem repeats are selected from the group consisting of microsatellites and minisatellites, or combinations thereof.

23. The method of clause 22 wherein the variable number tandem repeats are microsatellites and the microsatellites are STRs.

24. The method of clause 23 wherein the STRs have repeats of from about 2 to about 10 nucleotides.

25. The method of clause 23 wherein the STRs have repeats of from about 2 to about 8 nucleotides.

26. The method of clause 23 wherein the STRs have repeats of from about 2 to about 6 nucleotides.

27. The method of clause 23 wherein the STRs have repeats of from about 3 to about 5 nucleotides.

28. The method of clause 23 wherein the STRs have repeats of about 4 nucleotides.

29. The method of clause 22 wherein the variable number tandem repeats are minisatellites.

30. The method of clause 29 wherein the minisatellites have repeats of from about 9 to about 80 nucleotides.

31. The method of any one of clauses 1 to 30 wherein the purpose of the identification of the repeating sequences is selected from the group consisting of genetic mapping, linkage analysis, evolutionary history mapping, animal pedigree analysis, population identification, identification of ancestral origin or kinship, metagenomic analysis, and the identification of an individual by DNA matching, or combinations thereof.

32. The method of clause 31 wherein the purpose of the identification of the repeating sequences is the identification of an individual by DNA matching.

33. The method of clause 32 wherein the identification of an individual by DNA matching is selected from the group consisting of determining a familial relationship, determining the identity of a criminal, determining the identity of a deceased individual, or a combination thereof.

34. The method of clause 32 wherein the identification of an individual by DNA matching is for determining the identity of a criminal.

35. The method of clause 32 wherein the identification of an individual by DNA matching is for determining a familial relationship.

36. The method of clause 35 wherein the familial relationship is paternity.

37. The method of clause 31 wherein the purpose of the identification of repeating sequences is to determine the ancestral origin of an individual.

38. The method of clause 31 wherein the purpose of the identification of repeating sequences is to determine the kinship of an individual.

39. The method of clause 31 wherein the purpose of the identification of repeating sequences is population identification to determine the common STR variants in a population.

40. The method of clause 31 wherein the purpose of the identification of repeating sequences is metagenomic analysis to assess the biodiversity and the composition of a biological material in an environmental sample.

41. The method of any one of clauses 1 to 40 wherein the repeating sequences repeat from about 2 to about 75 times.

42. The method of clause 23 wherein the STRs are selected from the group consisting of simple repeats, compound repeats, complex repeats, and hypervariable repeats.

43. The method of any one of clauses 1 to 42 wherein the target nucleic acid is obtained from a body tissue or a fluid sample from an individual.

44. The method of clause 43 wherein the body tissue or the fluid sample is selected from the group consisting of a buccal sample, a blood sample, a saliva sample, a semen sample, a vaginal sample, a skin sample, a hair sample, a forensic sample collected from an environmental source, and a biopsy sample.

45. The method of clause 19 wherein the nucleic acid is DNA and the DNA is a mitochondrial DNA or a nuclear DNA.

46. The method of clause 31 wherein the genetic mapping or the linkage analysis is for screening for a disease with a genetic basis.

47. The method of any one of clauses 1 to 46 wherein the WPD analysis generates characteristic patterns from the periodic signal data which allow the periodic signal data to be differentiated from the non-periodic signal data.

48. The method of clause 47 wherein the characteristic patterns are characteristic of the type and the repetitive nature of the repeating sequences in the target nucleic acid.

49. The method of clause 1 wherein the method is used to identify a single nucleotide polymorphism (SNP) by identifying a marker or a sequence string near the SNP allowing for classification and identification of the SNP.

50. The method of any one of clauses 1 to 49 wherein the periodic signal data is obtained from a nucleic acid read that has non-repeating sequences on either flank of the repeating sequence.

51. A method for classifying sequencer reads for the presence or absence of repeating sequences wherein the repeating sequences are from a target nucleic acid, the method comprising the step of
sequencing the target nucleic acid to obtain sequence data wherein the sequence data is digitized and the digitized sequence data is decomposed using WPD, wherein the WPD generates data comprising non-periodic signal data and periodic signal data comprising coefficients, wherein the non-periodic signal data is classified into a non-repeat bin, and wherein the periodic signal data is placed in a repeat bin.

52. The method of clause 51 wherein the repeating sequences comprise different loci.

53. The method of any one of clauses 51 to 52 wherein the target nucleic acid comprises more than one allele for each of the repeating sequences in the target nucleic acid.

54. The method of any one of clauses 51 to 53 wherein the target nucleic acid is a DNA or RNA.

55. The method of any one of clauses 51 to 54 wherein the repeating sequences are tandem repeats.

56. The method of clause 55 wherein the tandem repeats are variable number tandem repeats.

57. The method of clause 56 wherein the variable number tandem repeats are selected from the group consisting of microsatellites and minisatellites, or combinations thereof.

58. The method of clause 57 wherein the variable number tandem repeats are microsatellites and the microsatellites are STRs.

59. The method of clause 58 wherein the STRs have repeats of from about 2 to about 10 nucleotides.

60. The method of clause 58 wherein the STRs have repeats of from about 2 to about 8 nucleotides.

61. The method of clause 58 wherein the STRs have repeats of from about 2 to about 6 nucleotides.

62. The method of clause 58 wherein the STRs have repeats of from about 3 to about 5 nucleotides.

63. The method of clause 58 wherein the STRs have repeats of about 4 nucleotides.

64. The method of clause 57 wherein the variable number tandem repeats are minisatellites.

65. The method of clause 64 wherein the minisatellites have repeats of from about 9 to about 80 nucleotides.

66. The method of any one of clauses 51 to 65 wherein the repeating sequences repeat from about 2 to about 75 times.

67. The method of clause 58 wherein the STRs are selected from the group consisting of simple repeats, compound repeats, complex repeats, and hypervariable repeats.

68. The method of any one of clauses 51 to 67 wherein the target nucleic acid is obtained from a body tissue or a fluid sample from an individual.

69. The method of clause 68 wherein the body tissue or the fluid sample is selected from the group consisting of a buccal sample, a blood sample, a saliva sample, a semen sample, a vaginal sample, a skin sample, a biopsy sample, or a latent DNA sample collected from the environment.

70. The method of clause 54 wherein the nucleic acid is DNA and the DNA is a mitochondrial DNA or a nuclear DNA.

71. The method of any one of clauses 51 to 70 wherein the WPD analysis generates characteristic patterns from the periodic signal data which allow the periodic signal data to be differentiated from the non-periodic signal data.

72. The method of clause 71 wherein the characteristic patterns are characteristic of the type and the repetitive nature of the repeating sequences in the target nucleic acid.

73. The method of any one of clauses 51 to 72 wherein the periodic signal data is obtained from a nucleic acid read that has non-repeating sequences on either flank of the repeating sequence.

BRIEF DESCRIPTION OF THE DRAWINGS

FIG. 3 discloses SEQ ID NO: 4.

DETAILED DESCRIPTION OF ILLUSTRATIVE EMBODIMENTS

In one embodiment of the invention, the method described herein is a classification operating on digitized sequences (e.g., the nucleotide sequence from a target nucleic acid) that distinguishes those sequences containing a periodic signal from those that do not. In one embodiment, the classification decision for acceptance or rejection of a sequence uses the magnitude of coefficients, or power, from a WPD that is applied to each sequence. As used herein, the term "nucleotide sequence" refers to symbolic representations of nucleotides arranged in sequential fashion. Typically, these symbolic representations of nucleotides are letters or numbers, and the arrangement is in the form of a word or a vector, respectively. A nucleotide sequence represented as a set of numbers arranged in a vector is referred to herein as a "digitized sequence". The term "periodic signal" describes the presence of two or more copies of a subsequence of symbols appearing adjacent to each other within the nucleotide sequence.

WPD is a method used to decompose a real-valued signal into a set of coefficient vectors. Each coefficient vector corresponds to a particular signal frequency range, and the coefficients in the vector contain a measure of the correlation between the original signal and a shifted and scaled version of a wavelet function. Generally speaking, a wavelet function is an oscillating function, usually with compact support, that begins and ends with value zero. Further restrictions are typically placed on such functions, including absolute and square integrability, and are application specific. As used herein, the term "WPD" can also refer to a recursive application of low and high pass quadrature mirror filters, where the filtered signal is taken as the coefficient vector. This alternate formulation of the WPD is well-known in the art (Vidakovic, 1999).

Figure 1:
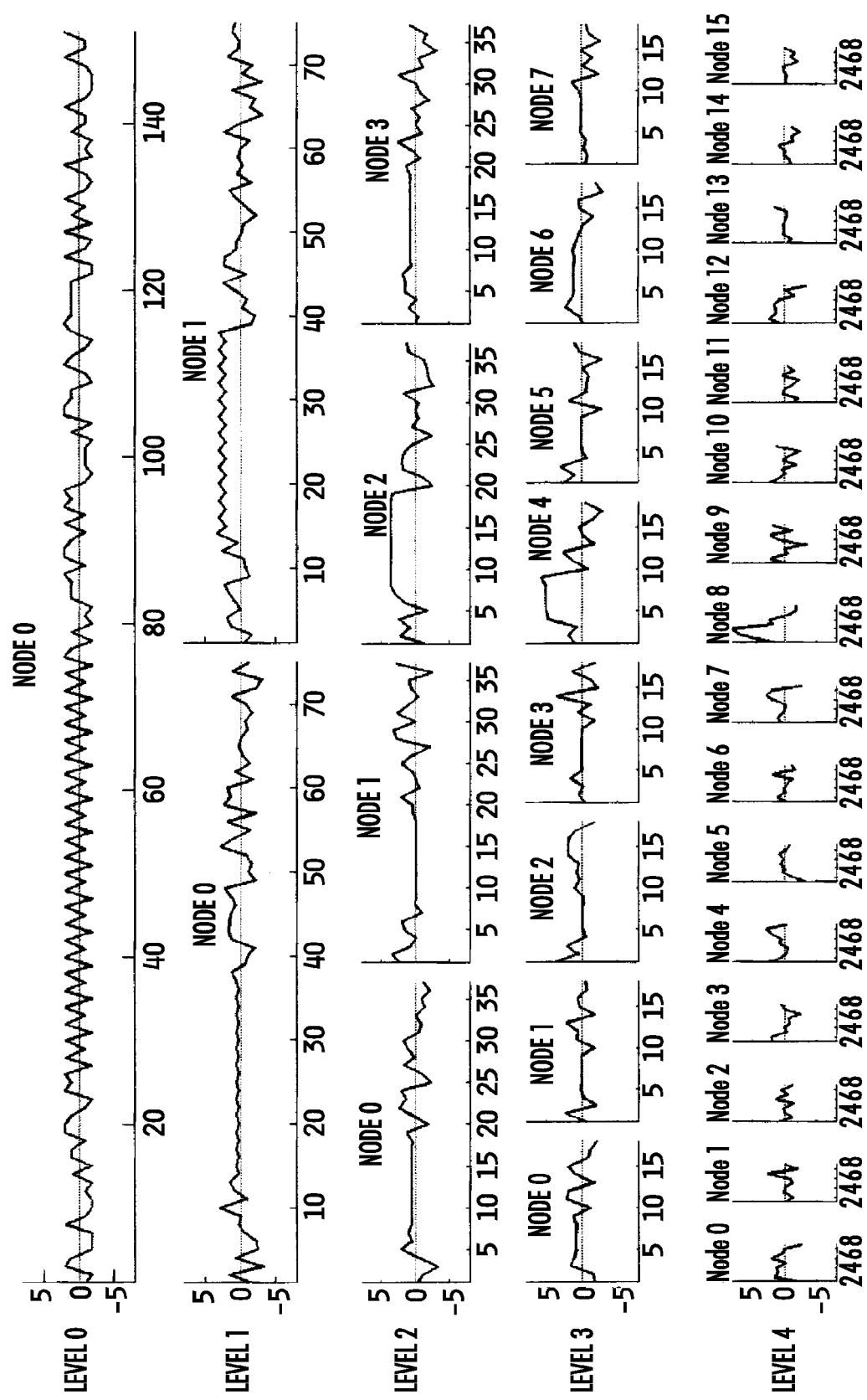
FIG. 1 shows a sample of the digitization of one allele of the D3S1358 STR locus and full WPD. Level 0 corresponds to the digitized short read and each subsequent level corresponds to the decomposition of the preceding level into detail and scale coefficients. Note the strong peak in Level 4 node 8 corresponding to the high frequency repeat pattern.

An example of WPD is given in FIG. 1. In this figure, the original digitized sequence appears in Level 0, Node 0 (top of figure). The sequence is processed using a low and high pass filter, producing Nodes 0 and 1 in Level 1, respectively. These two nodes are each processed using the same two filters again, resulting in Nodes 0-3 in Level 2. This process is recursively applied to subsequent nodes down to Level 4. In the particular example shown in FIG. 1, the low and high pass filters are quadrature mirror filters based on a Daubechies 4 wavelet function—however, in principle any such filters could be used. In addition, while the decomposition was only computed down to the fourth level for this example, in principle it can be done down to the $\lfloor \log_2 n \rfloor^{th}$ level, where n is the length of the digitized sequence—that is, the largest integer power k such that $2^k \leq n$.

In one embodiment, the invention operates on digitized sequences one at a time. In this embodiment, for a given sequence, the presence or absence of a periodic signal is ascertained by using coefficients from the WPD along with a decision rule. Using the example shown in FIG. 1, a periodic signal exists in the digitized sequence, and spans roughly the $25^{th}$ through $75^{th}$ base pairs. This periodicity is reflected as a large peak in the wavelet coefficients found in Level 4, Node 8. A simple threshold on the maximum coefficient in this node can be applied to identify this digitized sequence as one that contains a periodic signal. If the threshold is properly chosen, other sequences that do not contain periodic signals would not have the characteristic peak in Level 4, Node 8, and the maximum coefficient in that node would not exceed the threshold. This is only one embodiment of the intended use of this invention. It is expected that for other applications, more complex decision rules (rather than simple thresholding), multiple sets of coefficients (rather than just a single node), and an arbitrary decomposition level may be combined in a filter for a given type of target periodic signal.

In one embodiment, the primary output of the method described herein is a boolean (true/false) variable indicating the presence or absence of a periodic signal in the digitized sequence. However, other embodiments are contemplated in which more detailed output from the WPD could be required. For example, one or more sets of coefficients (or some function of those coefficients) could be returned to aid in a subsequent task to identify which type of periodic signal is present in the digitized sequence.

In one embodiment, the invention is intended to be used as a classifier to reduce a large set of digitized sequences to a smaller number that contain periodic signals. One possible reason for doing this is to reduce computation time spent on future analysis steps (e.g., aligning the resulting repeating sequences identified to a reference sequence), although other potential uses are envisioned here as well. In other embodiments, any type of analysis performed on nucleotide sequences can occur after classifying (i.e., filtering) as described herein has taken place. These include, but are not limited to, alignment of sequences to a reference sequence, identification of periodic signals (e.g., for DNA matching), genetic mapping and linkage analysis (e.g., for disease diagnosis and studies), and applications in population genetics (e.g., pedigree analysis or evolutionary history mapping).

Figure 11:
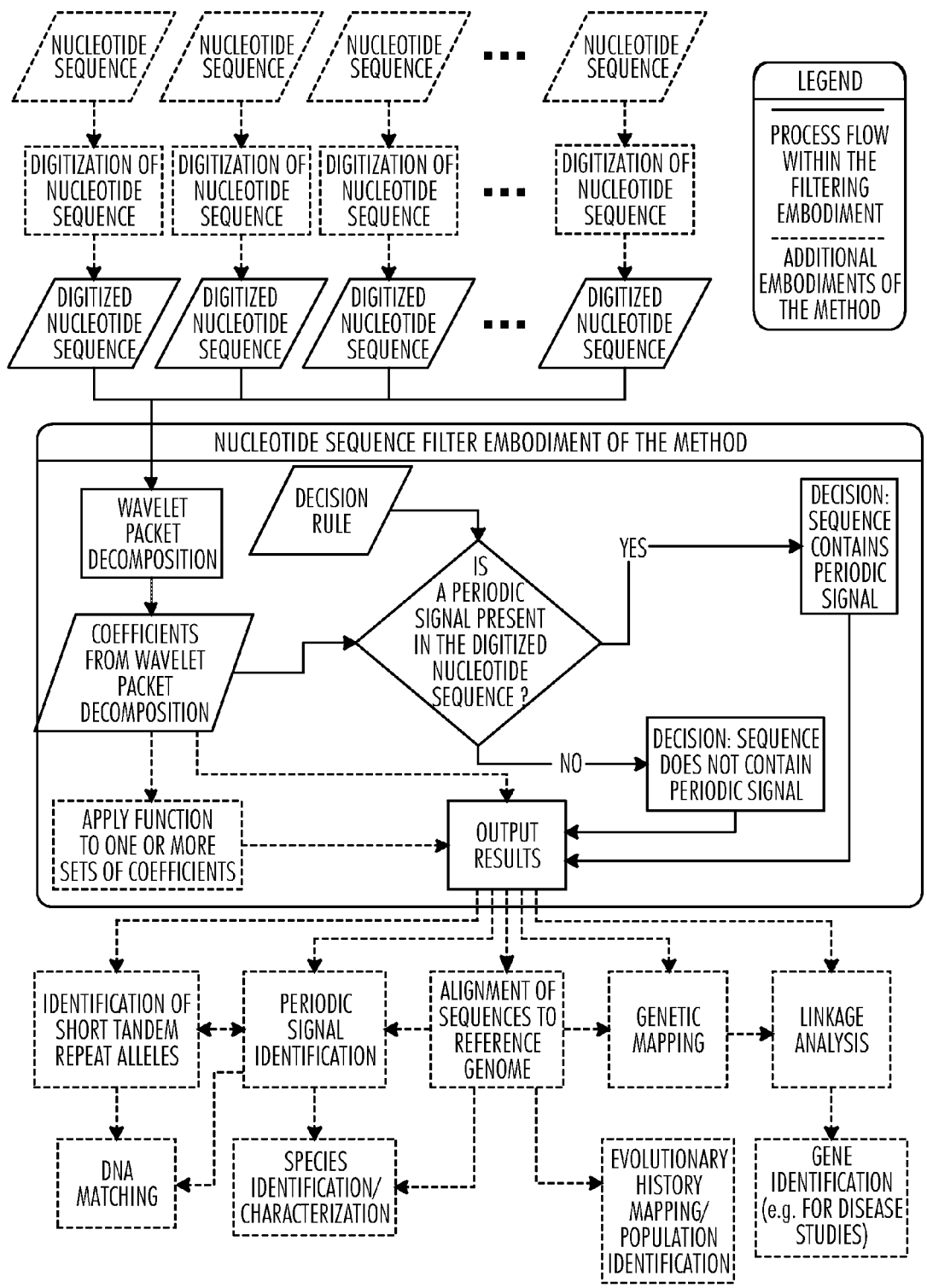
FIG. 11 shows a flowchart of illustrative embodiments of the method described herein.

A flowchart showing various embodiments of uses of the invention is shown in FIG. 11. The chart also shows potential steps in the methods described herein that could occur before or after the use of the classifying method described herein. These steps are not all necessary, nor are they an exhaustive representation of actions that could take place in relation to the classifying method.

In any of the various disclosures described in this application, the following features may be present where applicable, providing additional embodiments of the invention. A method is provided for identifying repeating sequences in a target nucleic acid comprising repeating sequences and non-repeating sequences. The method comprises the steps of sequencing the target nucleic acid to obtain sequence data wherein the sequence data is digitized and the digitized data is decomposed using WPD, wherein the WPD generates data comprising non-periodic signal data and periodic signal data comprising coefficients, wherein the non-periodic signal data is classified into a non-repeat bin, and wherein the periodic signal data is placed in a repeat bin, and identifying the repeating sequences in the target nucleic acid by matching the coefficients from the periodic signal data in the repeat bin to coefficients generated from WPD of a reference sequence. Compositions or articles of manufacture are also provided, such as computer programs (e.g., software) for use in the method. An example of pseudocode useful for performing the WPD described herein is provided in Example 5. It should be appreciated that in one embodiment, a computing device may be configured to perform all or a portion of the WPD described herein. For example, in an embodiment, a computing device may execute the pseudocode illustratively shown in Example 5 to perform the WPD described herein.

As discussed, a computing device may perform the WPD disclosed herein. As such, the disclosed embodiments may be implemented, in some cases, in hardware, firmware, software, or any combination thereof. The disclosed embodiments may also be implemented as instructions (e.g., the pseudocode illustratively shown in Example 5) carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

Figure 16:
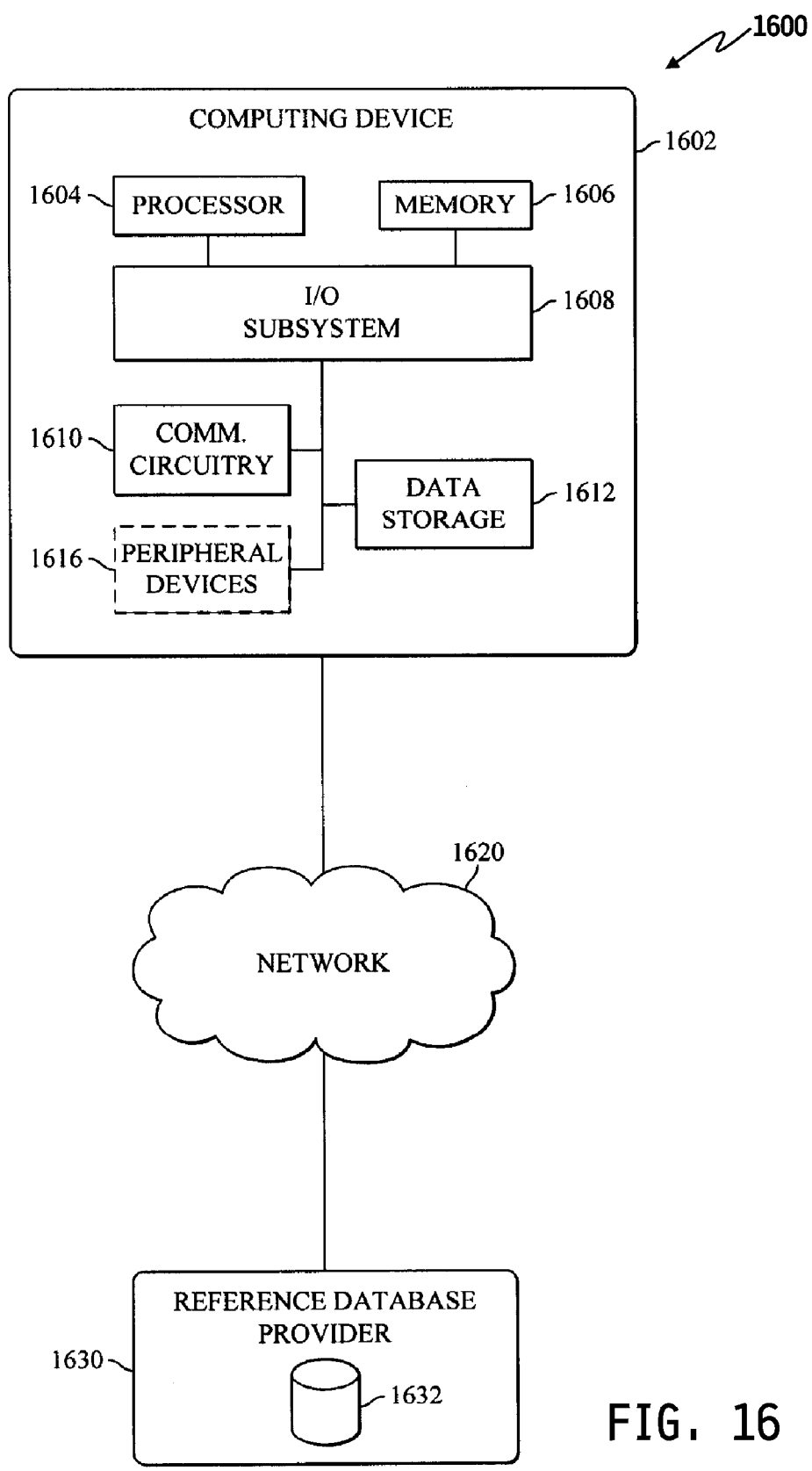
FIG. 16 shows an illustrative embodiment of a system for identifying repeating sequences in nucleic acids with a computing device.

Referring now to FIG. 16, an illustrative system 1600 for performing the WPD described herein includes a computing device 1602 and one or more reference database providers 1630. The computing device 1602 and the one or more reference database providers communicate with each other over a network 1680 to facilitate identifying sequences in a nucleic acid. Although only one reference database provider 1630 is shown in the illustrative system 1600 of FIG. 16, it should be appreciated that in other embodiments the system 1600 may include one, two, or more reference database providers 1630.

The computing device 1602 may be embodied as any type of computing device capable of performing the functions described herein including, but not limited to, a desktop computer, a laptop computer, a server, a tablet computing device, a smart phone, and/or any other type of computing device. The illustrative computing device 1602 includes a processor 1604, a memory 1606, an input/output subsystem 1608, communication circuitry 1610, and a data storage 1612. Of course, the computing device 1602 may include other or additional components, such as those commonly found in computing devices in other embodiments. Additionally, in some embodiments, one or more of the illustrative components may be incorporated in, or otherwise form a portion of, another component.

The processor 1604 may be embodied as any type of processor capable of performing the functions described herein. For example, the processor 1604 may be embodied as a single or multi-core processor(s), a digital signal processor, a microcontroller, or other processor or processing/controlling circuit. Similarly, the memory 1606 may be embodied as any type of volatile or non-volatile memory or data storage capable of performing the functions described herein. In operation, the memory 1606 may store various data and software used during operation of the computing device 1602 such as operating systems, applications, programs, libraries, and drivers. The memory 1606 is communicatively coupled to the processor 1604 via the I/O subsystem 1608, which may be embodied as circuitry and/or components to facilitate input/output operations with the processor 1604, the memory 1606, the data storage 1612, and other components of the computing device 1602.

The communication circuitry 1610 may be embodied as one or more devices and/or circuitry for enabling communications with the reference database provider 1630. The communication circuitry 1610 may be configured to use any suitable communication protocol to communicate with the reference database provider 1630 over the network 1620 including, for example, cellular communication protocols, wireless data communication protocols, and/or wired data communication protocols.

The data storage 1612 may be embodied as any type of device or devices configured for short-term or long-term storage of data such as, for example, memory devices and circuits, memory cards, hard disk drives, solid-state drives, or other data storage devices. In some embodiments, the computing device 1602 may maintain digitized nucleic acid sequence data and/or output generated from the WPD described in more detail below. Of course, in other embodiments, computing device 1602 may maintain additional or other types of data in the data storage 1612.

Additionally, in one embodiment, the computing device 1602 may further include one or more peripheral devices 1616. Such peripheral devices 1616 may include any type of peripheral device commonly found in a computing device such as additional data storage, speakers, a hardware keyboard, input/output devices, peripheral communication devices, and/or other peripheral devices.

The reference database provider 1630 may be embodied as any type of database provider that provides reference sequence data for comparison. In one embodiment, the reference database provider 1630 may be embodied as, or may otherwise include, a nucleic acid database 1632 having the reference sequence data stored therein.

In another illustrative embodiment, a method is provided for classifying sequencer reads for the presence or absence of repeating sequences wherein the repeating sequences are from a target nucleic acid, the method comprising the step of sequencing the target nucleic acid to obtain sequence data wherein the sequence data is digitized and the digitized sequence data is decomposed using WPD, wherein the WPD generates data comprising non-periodic signal data and periodic signal data comprising coefficients, wherein the non-periodic signal data is classified into a non-repeat bin, and wherein the periodic signal data is placed in a repeat bin.

Tandem repeats are an example of repeating sequences that can be identified in accordance with the method described herein. In one illustrative embodiment, the tandem repeats are variable number tandem repeats. In another illustrative aspect, the variable number tandem repeats are selected from the group consisting of micro satellites and minisatellites, or combinations thereof. In other embodiments, the variable number tandem repeats can be microsatellites and the microsatellites can be STRs. In another illustrative aspect, the tandem repeats can be STRs and the STRs are selected from the group consisting of simple repeats (e.g., $[ATCT]_6$ (SEQ ID NO: 1)), compound repeats (e.g. $[TCTA]_1[TCTG]_1[TCTA]_{12}$ (SEQ ID NO: 2)), complex repeats (e.g., $[TCTA]_4[TCTG]_6[TCTA]_3$ $TA[TCTA]_3$ $TCA[TCTA]_2TCCA$ $TA[TCTA]_8$ (SEQ ID NO: 3)), and hypervariable repeats. An example of a repeating sequence (e.g., an STR) that can be analyzed in accordance with the method described herein is the D3S1358 allele that has the sequence $TCTA[TCTG]_3[TCTA]_{11}$ (SEQ ID NO: 4). Another example of an STR that can be analyzed in accordance with the method described herein is the $TPDX_6$ allele with the sequence $CACTG[AATG]_6TTTGG$ (SEQ ID NO: 5). Suitable loci that can be analyzed in accordance with the method described herein include, but are not limited to, the CSF1PO, FGA, THO1, TPDX, VWA, D3S1358, D5S818, D7S820, D8S1179, D13S317, D16S539, D18S379, D18S51, D21S11, SE33, D1S1656, D2S441, D2S1338, D6S1043, D10S1248, D12S391, D19S433, and D22S1045 loci. These STR loci are exemplary STR loci that can be identified in a target nucleic acid using the described method. However, the method described in this application can be used to identify any repeating sequence, including any STR.

In the embodiment where the tandem repeats are STRs, the STRs can have repeats of from about 2 to about 20 nucleotides, from about 2 to about 15 nucleotides, from about 2 to about 10 nucleotides, from about 2 to about 8 nucleotides, from about 2 to about 6 nucleotides, from about 2 to about 5 nucleotides, or from about 3 to about 5 nucleotides. In other illustrative embodiments, the nucleotide repeats can have repeats of about 2, about 3, about 4, about 5, about 6, about 7, or about 8 nucleotides. Typically, the tandem repeats are STRs and the repeating sequences comprise about 2 to about 6 nucleotides and are adjacent to each other.

In the embodiment where the tandem repeats are STRs, the STRs can have repeats of from 2 to 20 nucleotides, from 2 to 15 nucleotides, from 2 to 10 nucleotides, from 2 to 8 nucleotides, from 2 to 6 nucleotides, from 2 to 5 nucleotides, or from 3 to 5 nucleotides. In other illustrative embodiments, the nucleotide repeats can have repeats of 2, 3, 4, 5, 6, 7, or 8 nucleotides.

In yet another embodiment, the variable number tandem repeats are minisatellites, and the minisatellites have repeats of from about 9 to about 80 nucleotides. In additional embodiments the minisatellites have repeats of from about 9 to about 70 nucleotides, from about 9 to about 60 nucleotides, from about 9 to about 50 nucleotides, from about 9 to about 40 nucleotides, from about 9 to about 30 nucleotides, or from about 9 to about 20 nucleotides.

In yet another embodiment, the variable number tandem repeats are minisatellites, and the minisatellites have repeats of from 9 to 80 nucleotides. In additional embodiments the minisatellites have repeats of from 9 to 70 nucleotides, from 9 to 60 nucleotides, from 9 to 50 nucleotides, from 9 to 40 nucleotides, from 9 to 30 nucleotides, or from 9 to 20 nucleotides.

In one illustrative embodiment, the repeating sequences can repeat from about 2 to about 75 times. In other illustrative embodiments, the repeating sequences can repeat from about 5 to about 75 times, from about 2 to about 65 times, from about 2 to about 55 times, from about 2 to about 45 times, from about 2 to about 35 times, from about 2 to about 25 times, from about 2 to about 15 times, or from about 2 to about 10 times.

In one illustrative embodiment, the repeating sequences can repeat from 2 to 75 times. In other illustrative embodiments, the repeating sequences can repeat from 5 to 75 times, from 2 to 65 times, from 2 to 55 times, from 2 to 45 times, from 2 to 35 times, from 2 to 25 times, from 2 to 15 times, or from 2 to 10 times.

Although STRs are typically analyzed in accordance with the method described herein, any type of repeating sequences in a target nucleic acid can be analyzed. These repeating sequences include STRs and other types of variable number tandem repeating sequences such as minisatellites, and markers or a sequence string near a single nucleotide polymorphism (SNP) allowing for classification and identification of the SNP.

Although any type of repeating sequence can be identified using the method described herein, STRs are commonly used as genetic markers because they are highly polymorphic and stably inherited, making them useful for organism identification, or disease diagnosis or for determining if an individual has a predisposition for a disease, by using genetic mapping or linkage analysis. Efficiently identifying STRs within a genome is advantageous in genotyping and in identification of individuals because efficient identification of STRs allows for quicker and more accurate identity testing and disease diagnosis, for example, than can be achieved with presently used methods. The method described herein presents a novel approach, utilizing a mathematical technique known as WPD, to identify both the length and frequency of repeating sequences in nucleic acids.

Wavelets are mathematical objects which can be used to find local, periodic patterns within a larger signal. Repeating sequences, such as STRs, have an inherent periodicity. As such, WPD can be used to detect these periodic signals within a nucleic acid. Using WPD, a large array of nucleotide data can be quickly analyzed, and non-periodic data can be classified. This greatly reduces the amount of data which needs to be analyzed using traditional alignment software, leading to a more efficient alignment algorithm, and one less sensitive to misreads.

As mentioned above, the method described herein can be used in any type of identification of an individual, genetic mapping, linkage analysis, or in disease diagnosis or to determine if an individual has a predisposition for a disease. For example, the purpose of the identification of the repeating sequences in accordance with the method described herein can be selected from the group consisting of genetic mapping, linkage analysis, and the identification of an individual by DNA matching, or combinations thereof.

In another illustrative embodiment, the method described herein is used for the identification of individuals, their tribal ancestry, or their facial features based on DNA samples gathered on the battlefield. For example, information about various combinations of alleles could be used to determine the phenotype for eye color, or facial features. In another embodiment, using a combination of alleles near repeat patterns could be used for identifying tribal ancestry for a given DNA.

In the illustrative embodiment where the method is used for the identification of an individual by DNA matching, the identification can be selected from the group consisting of determining a familial relationship, determining the identity of a criminal, determining the identity of a deceased individual, or a combination thereof. In the embodiment where the identification of an individual by DNA matching is for determining a familial relationship, the familial relationship can be paternity (e.g., parent-child), maternity (e.g., parent-child), the identification of a sibling (e.g., sibling-sibling), or any other kinship relationship that requires determination. The ability to rapidly identify relationships between individuals by DNA matching can also be used in the identification of matches for organ transplantation.

In another aspect, the method described herein can be used for genetic mapping or linkage analysis to screen an individual for a disease with a genetic basis, or to diagnose a disease or to determine if an individual has a predisposition for a disease. An individual can be screened for diseases with a genetic basis such as Huntington's disease, neurofibromatosis, Marfan syndrome, hereditary nonpolyposis colorectal cancer, cystic fibrosis, sickle-cell disease, Tay-Sachs disease, Niemann-Pick disease, spinal muscular atrophy, hemophilia, muscular dystrophy, and Lesch-Nyhan syndrome. An individual can also be diagnosed for any of these diseases, or any other disease with a genetic basis, using the methods and compositions described herein.

The target nucleic acid for use in accordance with the invention can be any nucleic acid that can be isolated and sequenced, such as mitochondrial DNA, nuclear DNA, or RNA. The target nucleic acid can be obtained from a body tissue, from a fluid sample from an individual, or from an object that the individual or the tissues or bodily fluid of the individual physically contacted and then can be prepared for sequencing. In various embodiments the body tissue or fluid sample is selected from the group consisting of a buccal sample, a blood sample, a saliva sample, a semen sample, a vaginal sample, a skin sample, a hair sample, a latent DNA forensic sample, and a biopsy sample. In embodiments where to goal is bioagent identification the sample could be a soil sample, an environmental swab, an air sample, or other suitable sample types.

In various other illustrative embodiments, body fluids that can be used in accordance with this invention include, but are not limited to, urine, nasal secretions, nasal washes, inner ear fluids, bronchial lavages, bronchial washes, alveolar lavages, pleural fluids, tears, gastric secretions, reproductive tract secretions, such as seminal fluid, lymph fluid, and whole blood, serum, or plasma. In various embodiments, tissue samples can include tissue biopsies and autopsy specimens. As used herein, the term "tissue" includes, but is not limited to, biopsies, autopsy specimens, cell extracts, tissue sections, aspirates, tissue swabs, and fine needle aspirates.

In various embodiments, sample preparation (i.e., preparation of the target nucleic acid) can involve rupturing cells (e.g., cells of the tissue or body fluid) and isolating the nucleic acid, such as DNA, from the lysate. Techniques for rupturing cells and for isolation of DNA are well-known in the art. For example, cells may be ruptured by using a detergent or a solvent, such as phenol-chloroform. The nucleic acid, such as DNA, may be separated from the lysate by physical methods including, but not limited to, centrifugation, pressure techniques, or by using a substance with affinity for the nucleic acid, such as, for example, silica beads. After sufficient washing, the isolated nucleic acid may be suspended in either water or a buffer. In other embodiments, commercial kits are available, such as Quiagen™, Nuclisensm™, Wizard™ (Promega), and Promegam™ to isolate a target nucleic acid for sequencing. Methods for isolating DNA are described in Sambrook et al., "Molecular Cloning: A Laboratory Manual", Cold Spring Harbor Laboratory Press, incorporated herein by reference. Other methods for preparation of DNA samples are well-known in the art.

After isolation, the target nucleic acid is sequenced. Methods for sequencing nucleic acids are also well-known in the art and are described in Sambrook et al., "Molecular Cloning: A Laboratory Manual", Cold Spring Harbor Laboratory Press, incorporated herein by reference. The target nucleic acid that is sequenced in accordance with the method described herein can contain both repeating and non-repeating sequences. In one illustrative embodiment, multiple short nucleotide reads are sequenced. For example, from about 1 to about 1000, from about 1 to about 500, from about 1 to about 200, or from 1 to about 100 short nucleotide reads, or any other useful range of short nucleotide reads can be sequenced.

In accordance with the method described herein the resulting sequence data is digitized for subsequent WPD analysis. In one embodiment, prior to WPD, the individual nucleotides must be digitized. The digitization encoding assigns a unique numeric value to each nucleotide type (e.g., A, C, G, and T) within a nucleic acid sequence. Exemplary encoding includes, for example, $-1.5$, $-0.5$, $0.5$, and $1.5$ or $-1$, $-2$, $1$ and $2$ assigned to A, C, G, and T, respectively. However, any type of digitization can be used and any digitization method is contemplated in accordance with the method described herein.

In one illustrative embodiment, the digitized sequence data is analyzed using WPD. Methods and algorithms for WPD are well-known in the art and illustrative methods are described in the Examples section in this application. In one embodiment, the WPD analysis generates periodic signal data and non-periodic signal data. In an illustrative aspect, to reduce the amount of data that needs to be analyzed using traditional alignment software, leading to a more efficient alignment algorithm, and one less sensitive to misreads, the non-periodic signal data is classified into a non-repeat bin, and the periodic signal data is placed in a repeat bin for analysis as described herein. In one embodiment, the periodic signal data can be obtained from a nucleic acid read that has non-repeating sequences on either flank of a repeating sequence.

In one illustrative aspect, the repeating sequences in the target nucleic acid are identified by matching the periodic signal data in the repeat bin to a reference sequence (e.g., an in silico genome). In one embodiment, the reference sequence can contain non-repeating sequences on either flank of a repeating sequence. In another embodiment, the reference sequence includes the portions of a genome corresponding to STR loci and the surrounding flanking DNA, enumerated for possible alleles of each STR. In another embodiment, the periodic signal data in the repeat bin can be matched to the reference sequence using an alignment algorithm. In this embodiment, WPD data obtained from the target nucleic acid can be compared to WPD data obtained from the reference sequence. In yet another illustrative embodiment, data generated from matching the periodic signal data to the reference sequence provides information selected from the group consisting of the location, the frequency, and the length of the repeating sequences, or a combination thereof, in the target nucleic acid.

The information regarding the location, the frequency, and the length of the repeating sequences, or a combination thereof, in the target nucleic acid can then be compared to data in a nucleic acid database, such as a DNA database, for use for any of the purposes described above such as identification of an individual, genetic mapping, linkage analysis, or in disease diagnosis or to determine if an individual has a predisposition for a disease.

In one embodiment, the DNA database can be a national government DNA database for use in criminal investigations. In one aspect, the database is selected from the group consisting of CODIS (i.e., U.S.), NDNAD (i.e., Europe), and FNAEG (i.e., France). In one illustrative embodiment, the database is CODIS. The CODIS database is used by the Federal Bureau of Investigation in the U.S. for identification of criminals. The CODIS database is a DNA database and currently contains sequence information for about 13 STR loci. In another illustrative embodiment, the database is the European NDNAD. The NDNAD database is a DNA database and currently contains sequence information for about 10 STR loci. In one aspect of the methods described herein, the sequence information in these DNA databases can change. For example, the sequence information for STR loci can vary from about 7 to about 16 STR loci. The STR loci for which sequence information is stored in several DNA databases is shown in Table 3. In another illustrative embodiment, the database is GenBank and WPD analysis data obtained by the method described herein can be compared to GenBank for use, for example, in genetic mapping, linkage analysis, or in disease diagnosis or to determine if an individual has a predisposition for a disease. In other illustrative embodiments the database is EMBL, DDBJ or a similar government database, or a custom sequence database.

In one embodiment, a threshold algorithm can be applied during WPD to identify greater than 80% of STRs, greater than 85% of STRs, greater than 90% of STRs, or greater than 95% of STRs, for example. In one aspect, the computational complexity of the filter is between order N and order N log (N) computations where N is the length of the DNA short read. In illustrative embodiments, the analysis of a FASTQ formatted DNA sample takes from about 83 MB/s to about 125 MB/s seconds, about 56 MB/s to about 125 MB/s seconds, or about 71 MB/s to about 125 MB/s seconds on a modern computer with a 2.8 GHz CPU, for example, depending on the number of final reads passing the filter. In one aspect, the threshold can eliminate from about 90% to about 98% of the short reads.

In other embodiments, the methods described herein include the following examples. The examples illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLE 1

Numerical Encoding

Figure 4:
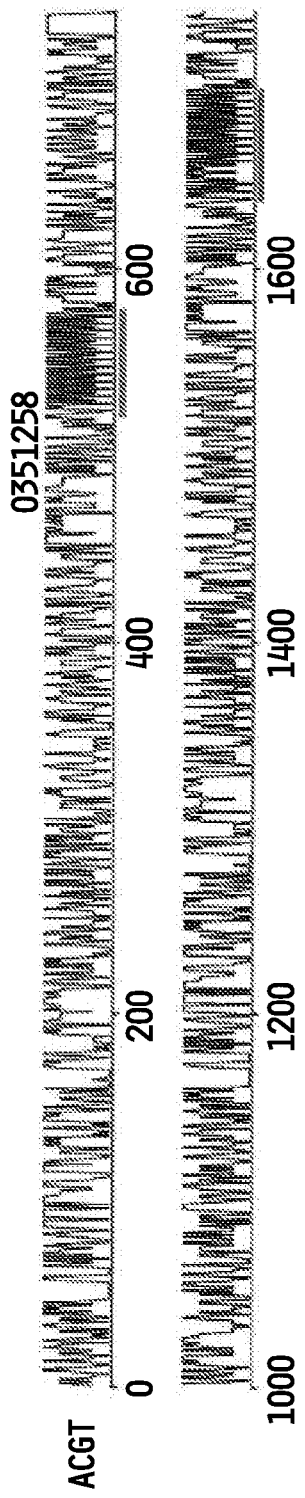
FIG. 4 shows the digitization of the D3S1358 locus.

Prior to applying wavelets to a DNA sequence, the individual nucleotides are digitized. The digitization encoding assigns a unique numeric value to each nucleotide type (A, C, G, and T) within a DNA sequence. Though the encoding is arbitrary. A simple linear encoding can be used, assigning numerical values (for example, −1.5, −0.5, 0.5, and 1.5 or −1, −2, 1 and 2) to (A, C, G, and T), respectively. The analysis that follows assigns (−1, −2, 1 and 2) to (A, C, G, and T), respectively, but other choices are clearly possible. FIG. 4 shows the partial digitization of the DS31358 STR locus sequence with two of the possible repeats, corresponding to two alleles at that locus, underlined.

WPD Basis

Next, the full WPD is performed on the STR locus and a wavelet basis is chosen to span the frequency and spatial extent of the locus. For this application the optimal basis is the one that provides the best separation in the power distribution between STR containing reads and those that do not contain STRs. This was determined empirically by examining the power distribution as a function of block size, wavelet node, and level of decomposition.

Characteristics of Periodic Region

Figure 5:
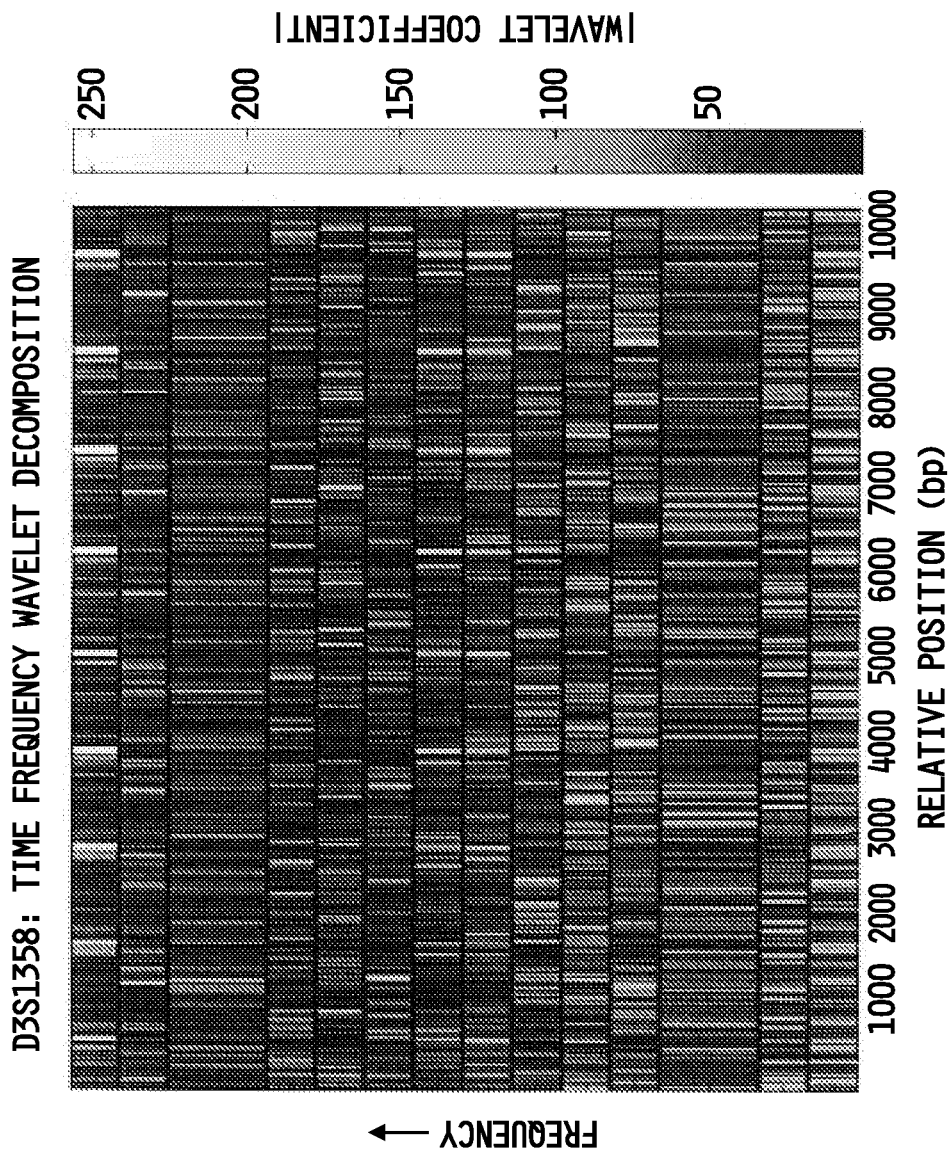
FIG. 5 shows the resulting coefficients for the selected basis for the D3S1358 locus.
Figure 6:
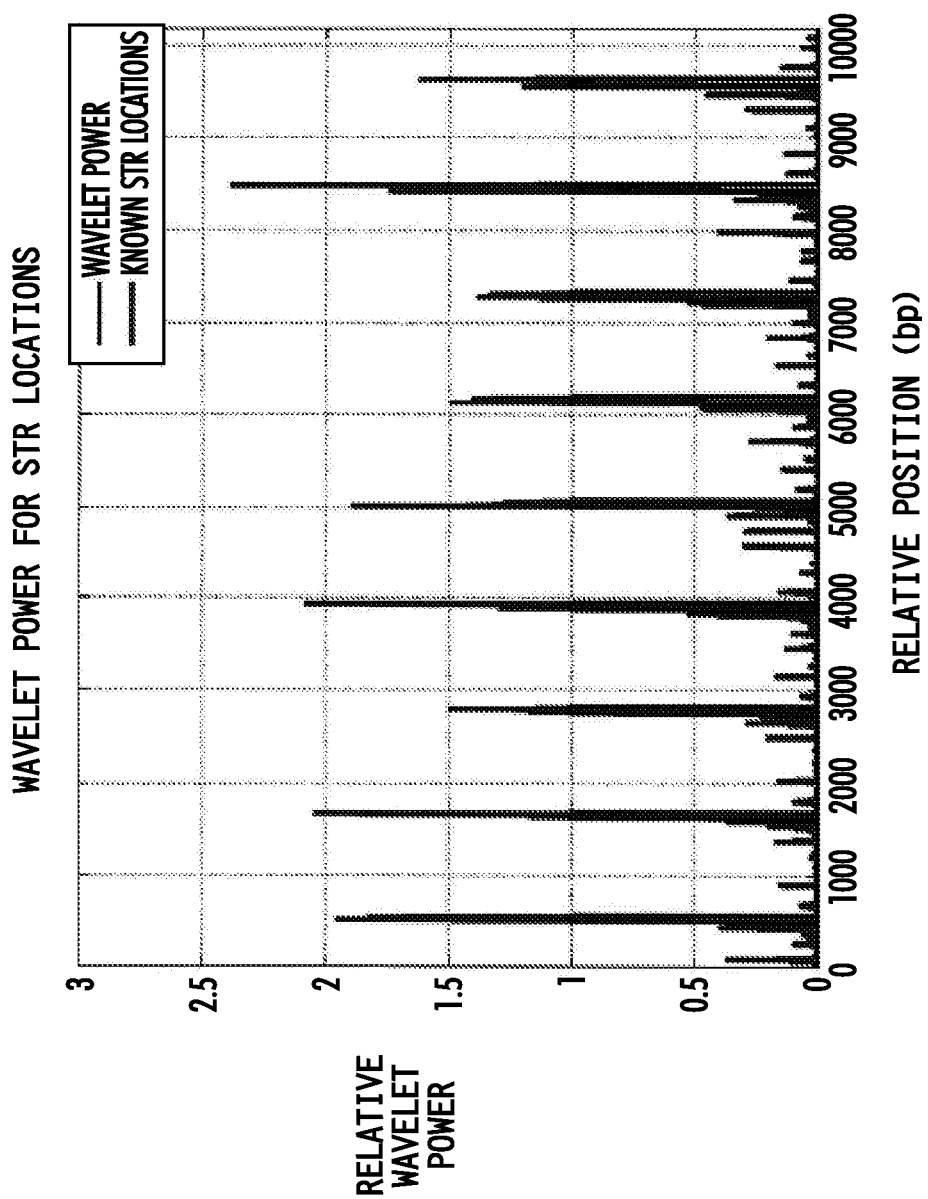
FIG. 6 shows a comparison of the periodicity in the signal from WPD to the alleles of the D3S1358 locus.

FIG. 6 shows the resulting coefficients for the selected basis for the DS31358 locus. Bright white regions correspond to some measure of periodicity in the signal. In this example, the alleles at the D3S1358 locus correspond to the bright regions on the top row of the image in FIG. 5. This relationship can be seen in FIG. 6. FIG. 6 shows the top row of the image in FIG. 5 in blue contrasted with the known STR locations in the reference sequence, shown in red. As is shown here there is a one-to-one correspondence between the STR location and regions of interest in the WPD of the D3S1358 locus. This suggests that a classifier can be developed using the WPD coefficients as a discriminator between STRs and non-STR regions.

Identification of STRs

Figure 10:
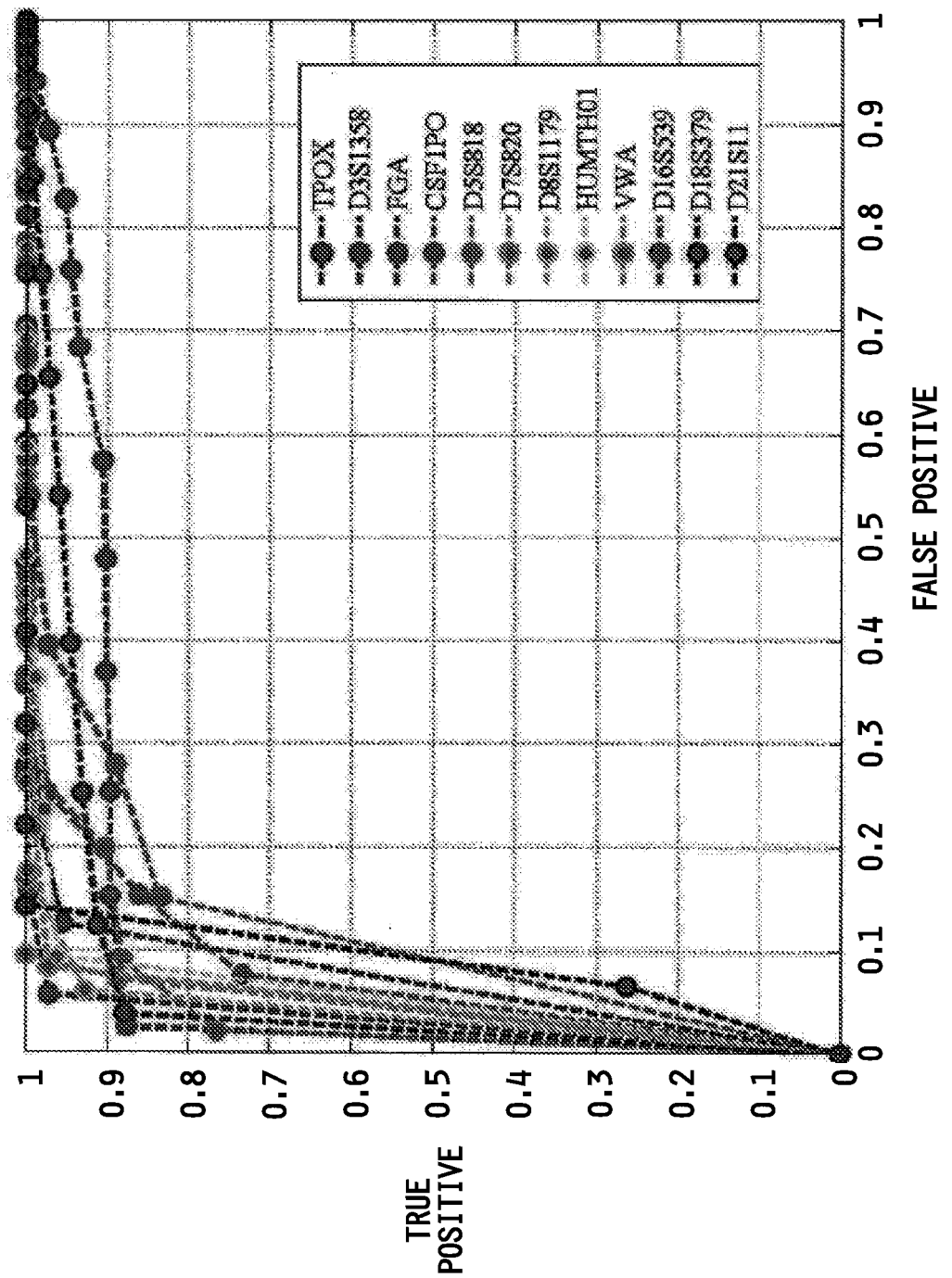
FIG. 10 shows a Receiver Operating Characteristic curve identifying better than 85% of true STRs with only a 15% False Positive.

With a WPD in place, and understanding of the characteristics of the wavelet coefficients known, a universal threshold can be put into place, and reads that do not pass the threshold can be removed from the sample for analysis. The background threshold can be varied and the number of correctly identified STRs can be measured, along with the number of misidentified STRs. The results of this threshold operation are shown in the Receiver Operating Characteristic (ROC) curve shown in FIG. 10. The threshold algorithm is applied to 12 STR loci, identifying more than 85% of true STRs (only 15% False Positive (FP)).

EXAMPLE 2

Steps for Classifying and Matching Short Tandem Repeats

In one embodiment, the steps for classifying STRs are as follows.
Numerically encode nucleotide data
Perform Wavelet transformation
Choose how to traverse the Wavelet Tree
Make Classification decision to maximize the STRs
Numerical Encoding
Prior to applying wavelets to a DNA sequence, the individual nucleotides may be digitized. The digitization encoding assigns a unique numeric value to each nucleotides type (A, C, G, and T) within a DNA sequence. Though the encoding is arbitrary, in one embodiment, a simple linear encoding is used, assigning numerical values (−1, −2, 1, 2) to (A, C, G, and T), respectively. In another embodiment, A, C, G, and T can be 2, −1, 1, and 2, respectively.

Wavelet Packet Decomposition

An example of full WPD is shown for the D3S1358 locus in FIG. 1. WPD was performed at each level to give the detail and scale coefficients for a given level. For each wavelet transformation, the detail coefficients correspond to high frequency components while the scale coefficients correspond to the low frequency components. The full decomposition to a given level can be organized in a series of frequency ordered nodes as shown in FIG. 1.

Traversing the Wavelet Tree

The power, or sum of squares, of a set of coefficients is largest in the repeat regions for all but two of the 13 CODIS STRs. For the classification application, only the nodes necessary to reach those nodes corresponding to STRs are calculated. This is done by either going to the nodes with the maximum power, or by selecting specific nodes within the WPD. The fourth level of the tree was chosen for its frequency resolution and spatial resolution given the size of the typical repeat pattern and the short read size of 151 base pairs in this particular example.

Classifying Reads

The coefficients at a given node correspond to given frequency range and scale. By choosing a threshold on a block of coefficients one can select for a contiguous repeat pattern at a given frequency. Optimization of the choice of the best classifier depends on the desired application and the algorithm is flexible to allow for the tradeoffs of higher purity versus a larger sample size of STRs.

A filter was constructed that performed the STR wavelet decompositions for only those nodes with larger power traversing the tree to the nodes with large coefficients, characteristic of the high frequency STR patterns. The Daubechies 4 wavelet was used for the decomposition and the $4^{th}$ level of the wavelet tree was selected.

Matching

Figure 2:
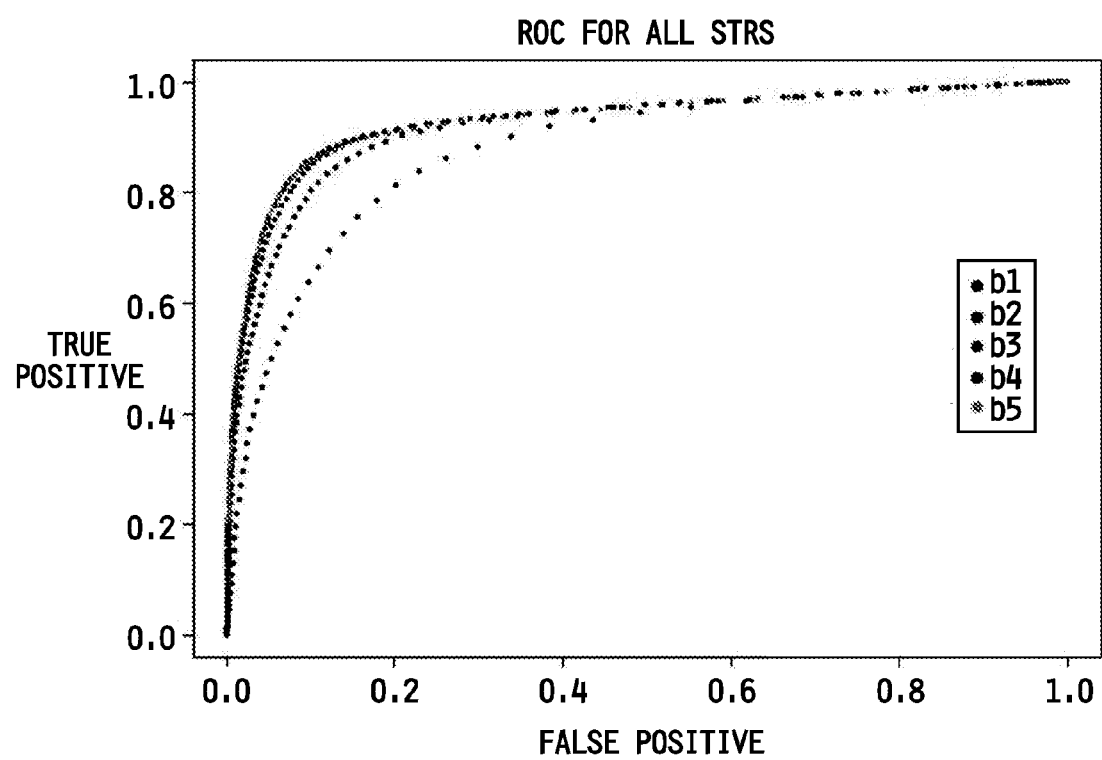
FIG. 2 is a plot showing the Receiver Operating Characteristic for a series of different block sizes and choices of filtering threshold as described in Example 1.

A constructed Monte Carlo (MC) dataset with all known alleles of the 13 CODIS STRs was created to allow for tuning the filter and a second MC dataset was constructed using non-STR sections of the human genome outside the STR repeat regions. Running over both sets of MC the performance of the true positive versus false positive rates was measured, as shown in FIG. 2. The current best filter achieved a true positive rate of 86.7% with a false positive rate of 10.9%.

EXAMPLE 3

This example shows a particular embodiment of the invention wherein the method described herein is used to classify nucleotide sequences drawn from an Illumina® next generation sequencer. The sequences, herein referred to as "short reads", are produced by first using a polymerase chain reaction (PCR) approach to amplify DNA. Next, the Illumina® sequencer, in concert with specially designed primers, is used to sample DNA in regions around the 13 FBI CODIS loci for STRs. These DNA samples, in this case 150 base pairs long, are the short reads. The short read is written as a sequence of the letters A, G, C, and T, corresponding to the purines adenine and guanine, and the pyrimidines cytosine and thymine. When a base call cannot be uniquely identified the letter N, corresponding to a generic nucleotide is used.

Figure 12:
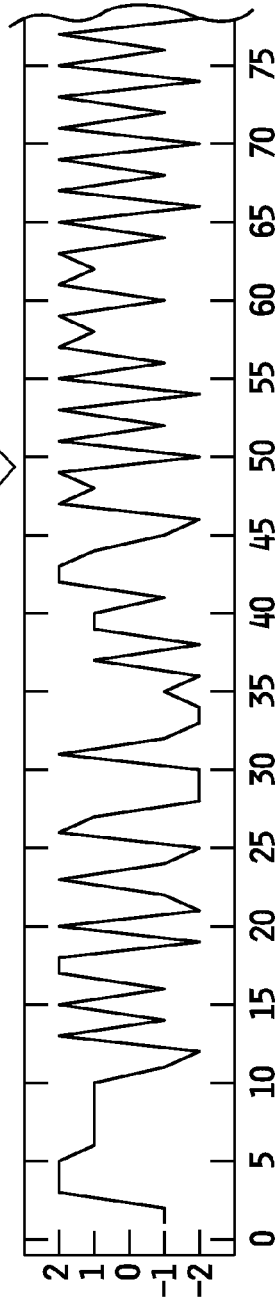
FIG. 12 shows the digitization of a nucleotide sequence, (SEQ ID NO: 72).
Figure 12:
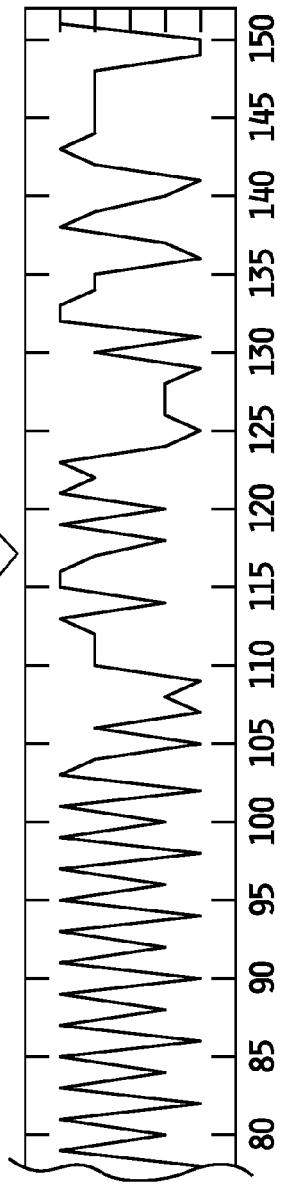

The short reads are then classified into two groups—those reads that contain periodic signals (i.e., some or all of an STR) and those that do not (i.e., reads from non-repeat flanking DNA regions). To prepare the reads for the classifier, they are first digitized. Although in principle any encoding could be used, in this case a simple substitution is used, where the numbers (−2, −1, 0, 1, 2) replace the letters A, C, N, G, and T, respectively. FIG. 12 shows an example of a read being digitized under this encoding.

Figure 13:
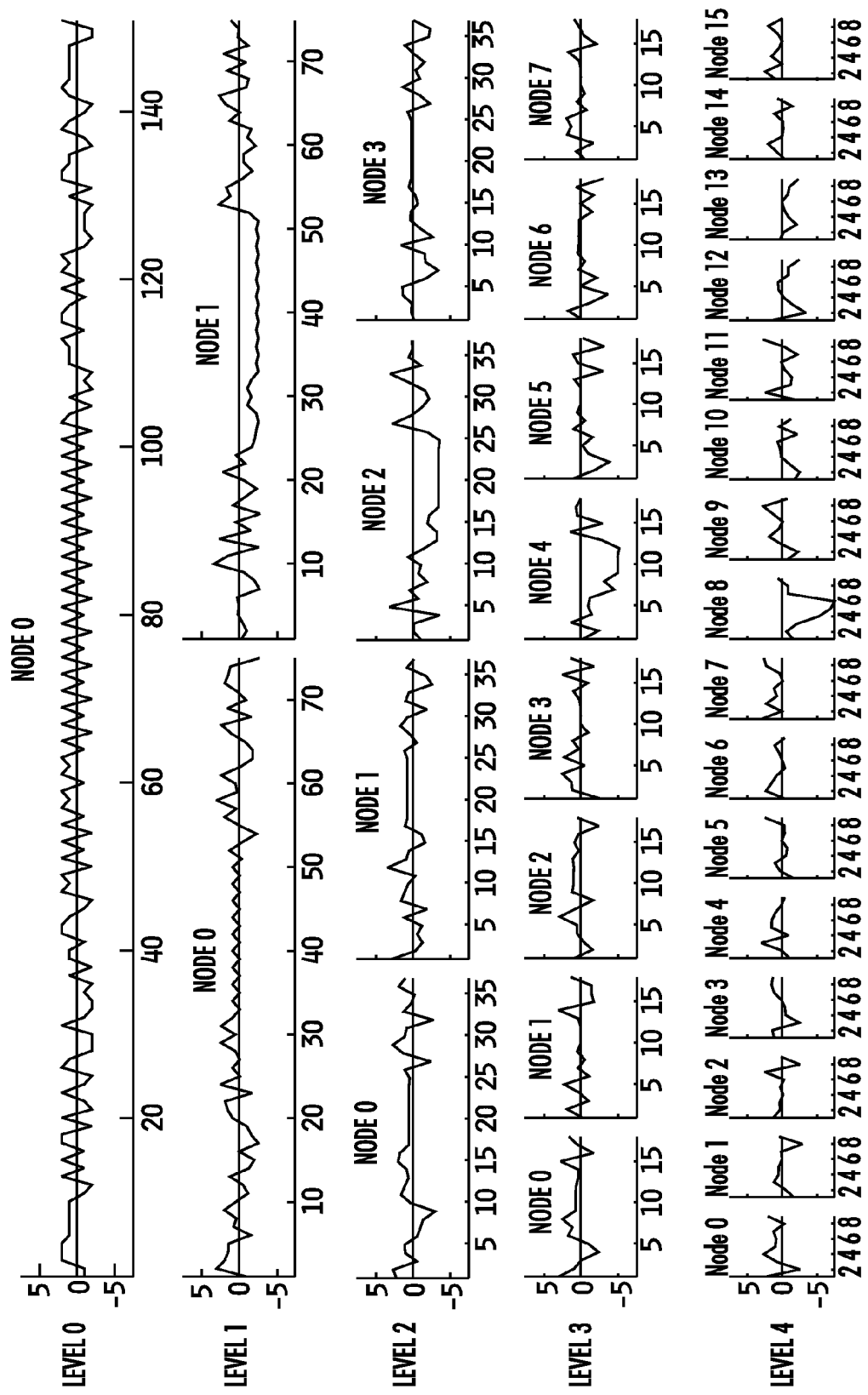
FIG. 13 shows the WPD for a short read containing a periodic signal.
Figure 14:
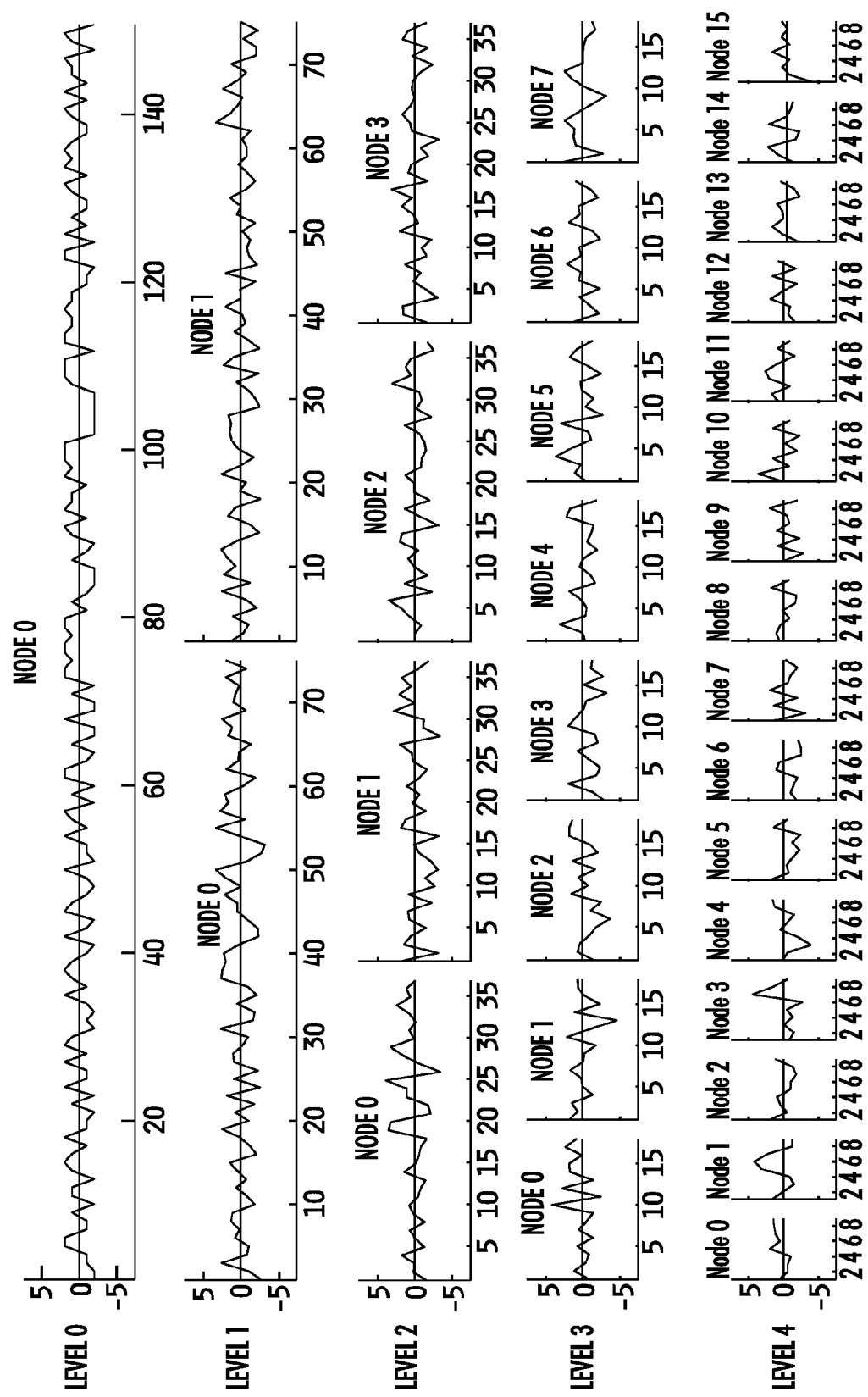
FIG. 14 shows the WPD for a short read that does not contain a periodic signal.

For each short read, a WPD is used to divide the read into sets of wavelet coefficients. The coefficients in each node of the tree correspond to the resonance of the digitized sequence at different periodic frequencies. The decomposition for the digitized read from FIG. 12 has been performed and displayed in FIG. 13. The original read appears in Level 0, Node 0 of the decomposition, and has a clear periodic signal (in this case, an STR of length 13) near the center of the sequence. This periodic signal resonates at a particular frequency corresponding to the node in Level 4, Node 8, where a large negative peak appears. In contrast, FIG. 14 shows an example of a WPD on a read that does not contain an STR. None of the peaks in the coefficients are as large as the one found in Level 4, Node 8 for the previous read.

Figure 15:
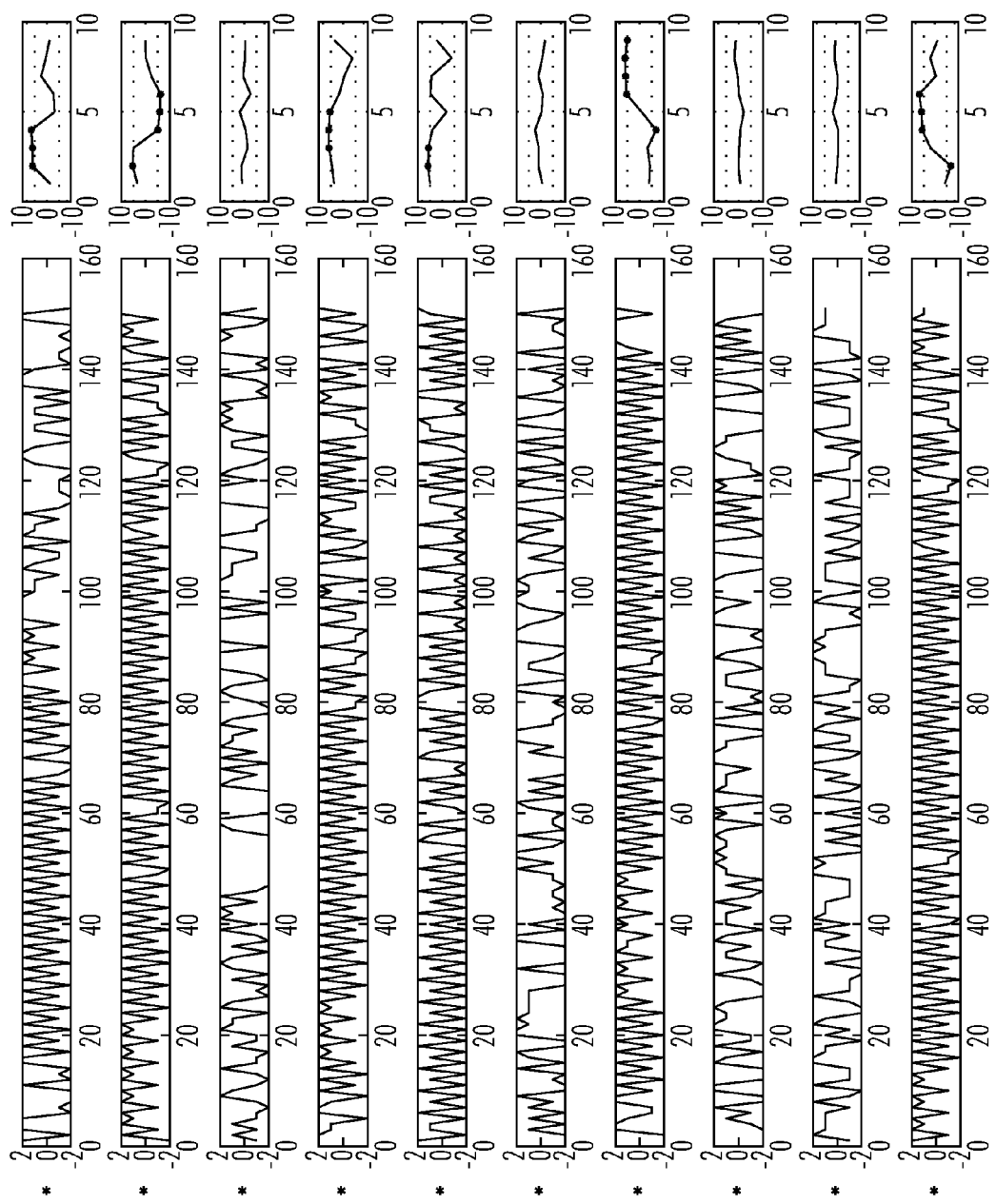
FIG. 15 shows examples of sequencer reads (left column) and the wavelet coefficients in Level 4, Node 8 (right column). Coefficients crossing the threshold (the dotted lines) are indicated with an asterisk. Reads with asterisks on the left contain STRs.

In this particular embodiment, a simple threshold on the coefficient with the maximum magnitude in Level 4, Node 8 may be used to decide whether a read contains an STR somewhere in the sequence. To improve performance, thresholds may be used on other nodes in Level 4 of the decomposition, since not all of the 13 FBI CODIS STR patterns resonate at the frequency in Node 8 of that level. FIG. 15 shows a sample of 10 short reads, some of which contain an STR and some that do not. The reads containing STRs are indicated by an asterisk on the left of the plot. The first column shows the digitized read, and the second column shows the wavelet coefficients from Level 4, Node 8. A threshold on the maximum magnitude coefficients appears as two dotted lines (one for the magnitude in either direction). Coefficients exceeding the threshold are marked with asterisks. The classifier separates this group of 10 reads into those that contain STRs (i.e., one or more coefficients exceeded the threshold) and those that do not (i.e., none of the coefficients exceeded the threshold).

EXAMPLE 4

Identifying STRs in the D3S1358 Locus

Figure 3:
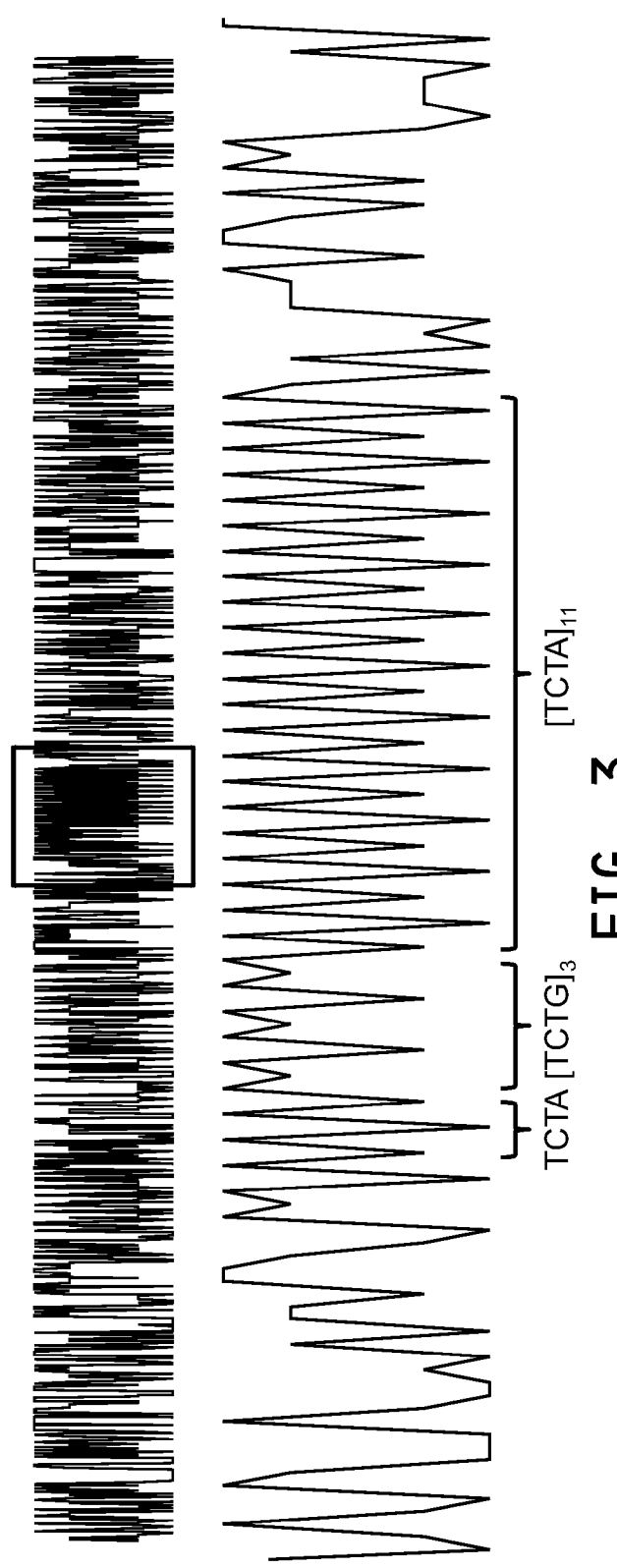
FIG. 3 shows a diagram of 1000 base pairs of reference genome centered on an STR.

The D3S1358 locus has an STR allele that is a 15-repeat variation containing TCTA[TCTG]3[TCTA]11 (SEQ ID NO: 4). Approximately 1000 base pairs of reference genome, centered on the STR, after wavelet packet decomposition is shown in FIG. 3. As an example, 151 base pair short reads can be processed. The reads are first digitized into numeric values. The partial digitization of the D3S1358 allele is shown in FIG. 4.

The wavelet packet decomposition is then performed. The full wavelet packet decomposition is performed on the sequence and a wavelet basis is chosen to span its frequency and spatial extent. Choosing the basis for the wavelet representation of the DNA signal determines the spatial and frequency resolution and impacts how well the STR-containing reads can be classified. The optimal basis for classifying STRs is the one that provides the best separation in the power distribution between STR containing reads and those that do not contain STRs. This was determined empirically by examining the power distribution as a function of block size, wavelet node, and level of decomposition.

FIG. 5 shows the resulting coefficients for the selected basis for the D3S1358 DNA sequence. Bright white regions correspond to some measure of periodicity in the signal. In this example, the alleles of the D3S1358 locus correspond to the bright regions on the top row of the image in FIG. 5. This relationship can be seen in FIG. 6. FIG. 6 shows the top row of the image in FIG. 5 in blue contrasted with the known STR locations in the reference sequence, shown in red. As is shown here there is a one-to-one correspondence between the STR location and regions of interest in the wavelet packet decomposition of the D3S1358 locus. This suggests that a classifier can be developed.

With wavelet packet decomposition in place, and an understanding of the characteristics of the wavelet coefficients, a universal threshold can be put into place, and zeros can be substituted to remove all non-periodic signal. The background threshold can be varied and the number of correctly identified STRs can be measured, along with the number of misidentified STRs.

Figure 7:
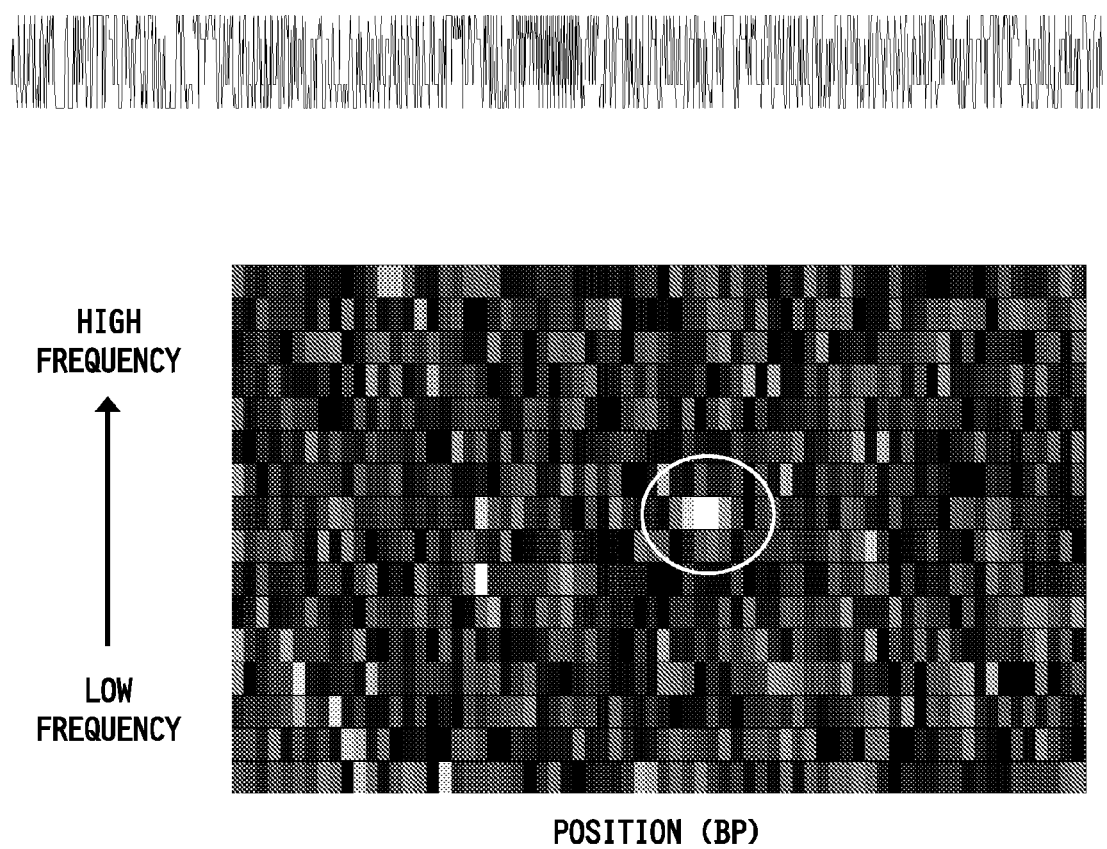
FIG. 7 shows a node where the coefficients spike at a repeat location in the D3S1358 locus.
Figure 8:
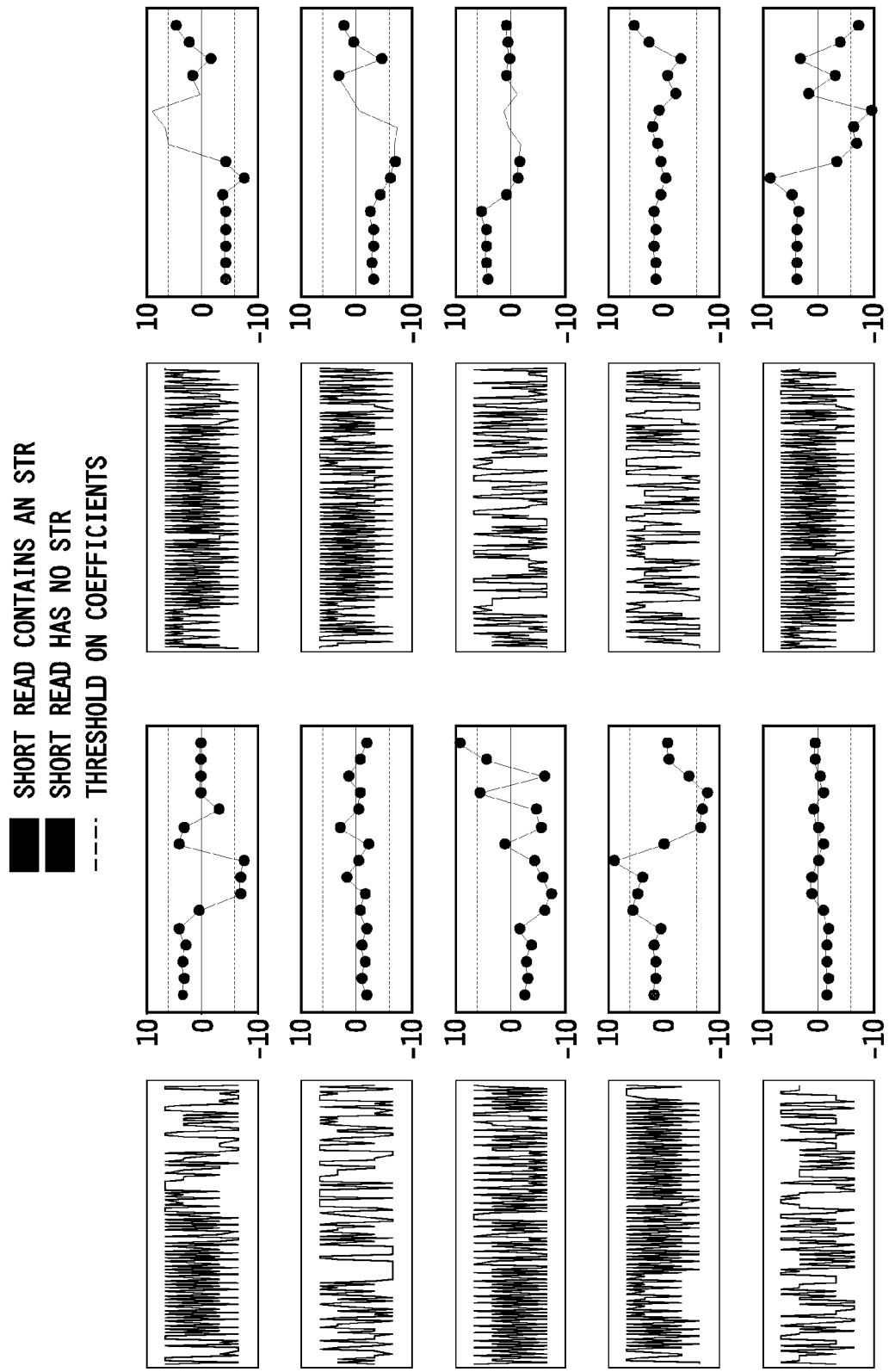
FIG. 8 shows exemplary short reads containing an STR, short reads without an STR, and the threshold on coefficients.

To put the threshold in place, the node sensitive to STR pattern is examined, following the decomposition. For each STR, there is a corresponding node where the coefficients spike at the repeat location as shown in FIG. 7. A coefficient threshold is applied to determine if a repeat is present. Short reads with repeats present continue to the STR matching step of the process. Other short reads are discarded. Different thresholds may be useful for different machines and DNA sequencing techniques. Examples of short reads containing an STR, short reads without any STRs, and the threshold on coefficients are shown in FIG. 8.

Figure 9:
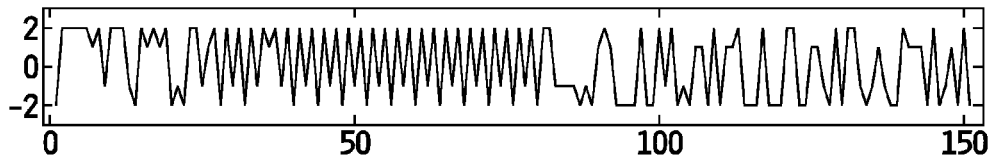
FIG. 9 shows exemplary matches of short reads to a reference sequence.
Figure 9:
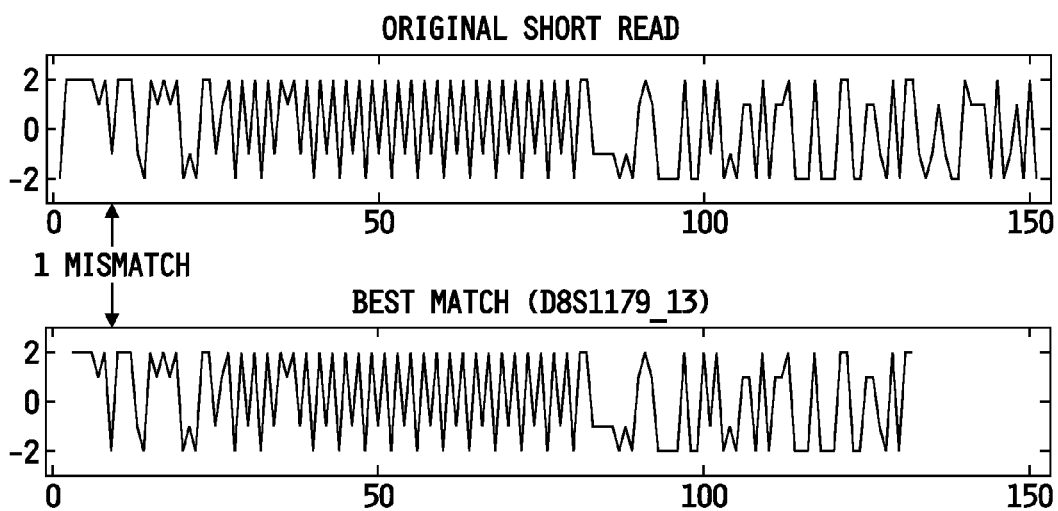

Short reads with repeats are fed into an STR matching algorithm to match reference genome repeat patterns for each STR and its variants. Flanking DNA is included in the reference genome to serve as an anchor. Matching is performed to determine which pattern matches the short read the best. Highly compatible matches are tracked and tallied. Most common matches reveal which STRs are present in the dataset as shown in FIG. 9. Exemplary results of this threshold operation are shown in the Receiver Operating Characteristic (ROC) curve shown in FIG. 10. The threshold algorithm is applied to 12 STR loci, identifying better than 85% of true STRs with only a 15% False Positive (FP).

EXAMPLE 5

Pseudocode

```
Main( ){
    Loop Lines of input files containing short reads{
        // Change G to 1, A to -1, T to 2, C to -2, and N 0
        // "N"s occur when there is not enough information to
        make a base call
        shortReadLine = ReadLine(file)
        numericLine = NumericEncode(shortReadLine)
        // Get coefficients of the node with STR in it
        // by going to the node with the most power (highest
        magnitude coefficients)
        // on the 4th level of the wavelet packet decomposition
        coeff = getNodeCeofficientsByPower(numericLine,
        4thLevel)
        // filter by using a threshold
        doesShortReadPass = filterOnCoefficients(coeff, threshold,
        blocksize)
        if(doesShortReadPass){
            writeOut(shortReadLine)
        }
        Next Line
    }
}
getNodeCoefficientsByPower(numericLine, treelevel){
// loop over the wavelet packet decomposition tree
// following the path that leads to nodes of higher power
// until reaching the desired tree level
    while(treeLevel >= 0){
        // Calculate the scale and detail coefficients of single
        decomposition
        db4(numericLine, scale, detail, numericLineSize)
        //Calculate the total power in the detail and scale
        coefficients
        Scalepower = 0;
        Detailpower = 0;
        Loop over all coefficients {
            ScalePower = ScalePower + scale_i^2
            DetailPower = DetailPower + detail_i^2
        }
        // Take the node with higher power as the new signal
        if (DetailPower > ScalePower){
            // swap the old signal with the detail coefficients
            numericLine = detail
        } else {
            // swap the old signal with the detail coefficients
            numericLine = scale
        }
        TreeLevel = TreeLevel - 1
        Next
    }
    // Return the coefficiences corresponding to the node with maximal
    power
    Return numericLine;
}
filterOnCoefficients(coeff, threshold, blocksize){
```

-continued

Pseudocode

```
// loops over the wavelet node coefficient and checks to see if
// a block of coefficients exceed a threshold
    isPassed = false;
    // only need to move the filter block along the coefficients
    loopSize = size - (blocksize - 1);
    // move the filter block along the coefficients and check if any
    // block is above the threshold
    Loop i in loopSize{
        bool isBlockPassing = true;
        loop j in blockSize{
            isBlockPassing = isBlockPassing &&
                coeff[i+j]*coeff[i+j] > threshold;
        }
        if (isBlockPassing){
            isPassed = true;
            break;
        }
    }
    return is Passed;
```

EXAMPLE 6

STR regions within genomic DNA (gDNA) may be selectively targeted and amplified using polymerase chain reaction (PCR) methods with nucleotide primers corresponding to regions surrounding the STRs. The following method was used to produce STR genetic material using gDNA as input. Nucleotide primers (Table 1 and Table 2) were prepared in working stocks solubilized in ddH$_2$O. An enzymatic reaction was set up by adding the following materials to a test tube: ddH$_2$O, high fidelity DNA polymerase (e.g. Taq or Pfu DNA polymerase), master mix containing buffering agent and MgCl$_2$ and nucleotides (dNTPs), 0.5 µM Primer A, 0.5 µM Primer B, and 50-750 ng template gDNA. A PCR reaction was performed using a thermal cycler and the following conditions: initial denaturation/activation at 98° C. for 30 seconds, denaturation at 98° C. for 10 seconds, anneal at 70° C. for 30 seconds, extension at 72° C. for 120 seconds, repeat denaturation, anneal and extension steps 30 times, polish (final) at 72° C. for 10 minutes, hold at 4° C. The enzymatic reaction may be purified, for example, using methods of gel electrophoresis, column purification (e.g. silica), or alcohol-salt precipitation. Purified material was next sequenced (e.g. high through-put sequencer) and the raw data analyzed as described herein.

Table 1 is a list of genetic sequences that represent the nucleotide primers synthesized for the purpose of selectively amplifying, by PCR, STR loci from genomic DNA (gDNA). Each row represents a separate genetic sequence and properties of the sequence. The ID number is an internal tracking number for the genetic sequence. The PCR reference (A or B) and strand on template represent the pair of sequences used for each PCR reaction, such that A, plus is always used with B, minus. Length is the total number of nucleotides contained in each primer sequence. Start and stop information designates the position (5') within the STR locus where the primers match the database sequence for the locus and whose difference is described as the amplicon size. Tm is the calculated melting temperature (° C.) of the primer as determined by the Primer BLAST utility (http://www.ncbi.nlm.nih.gov/tools/primer-blast/). GC % is the percentage of G or C nucleotides within the primer sequence which influences Tm and other physical properties of the primer, such as annealing temperature. The targeted STR locus is defined in the loci column. For Table 2, the nucleotide position describes where the STR repeat occurs within the sequence of the locus within the database and describes the relative position of the repeat (middle or end) within the amplicon. Each primer pair was validated for synthesis of amplicons on at least five human gDNA samples.

TABLE 1

| ID | SEQ ID NO: | Sequence | PCR Ref. | Strand on template | length | Start | Stop | Tm (Primer Blast) | GC% | Loci |
|---|---|---|---|---|---|---|---|---|---|---|
| VFD003 | 6 | TGTCGCGACTCCCCCTGTGT | A | Plus | 20 | 53210 | 53229 | 59.8 | 65.0% | TPOX |
| VFD004 | 7 | GGCCCGATCCCCTGACACCT | B | Minus | 20 | 54615 | 54596 | 60.0 | 70.0% | |
| VFD138 | 8 | GGGCCATCCCAGCCCTCTCA | A | Plus | 20 | 51387 | 51406 | 59.96 | 70.00% | |
| VFD139 | 9 | TGGCTGGGACCCCCTTTGCT | B | Minus | 20 | 53918 | 53899 | 60.03 | 65.00% | |
| VFD009 | 10 | TGCCGAGGCACAGAAGCGTG | A | Plus | 20 | 76742 | 76761 | 60.0 | 65.0% | D3S1358 |
| VFD010 | 11 | TGCCAGGGCACTGCTCCAGA | B | Minus | 20 | 77969 | 77950 | 60.1 | 65.0% | |
| VFD011 | 12 | GCCAGACCATGGCTGCTGGG | A | Plus | 20 | 76857 | 76876 | 60.0 | 70.0% | |
| VFD012 | 13 | TGCCCACTTCTGCCCAGGGA | B | Minus | 20 | 77925 | 77906 | 59.8 | 65.0% | |
| VFD025 | 14 | GGGCATGAATGAGGGCATGGCT | A | Plus | 22 | 3209 | 3230 | 59.5 | 59.1% | D21S11 |
| VFD026 | 15 | CATGCCATTTATGGGGCAACAGGT | B | Minus | 24 | 4774 | 4751 | 58.0 | 50.0% | |
| VFD029 | 16 | GAGGGCATGAATGAGGGCATGG | A | Plus | 22 | 3207 | 3228 | 57.7 | 59.1% | |
| VFD030 | 17 | ACAGCTCACTCCAAGGACAGCTGT | B | Minus | 24 | 4938 | 4915 | 59.8 | 54.2% | |
| VFD031 | 18 | AGCCGACAAAAGGCTATGCGCT | A | Plus | 22 | 75415 | 75436 | 58.6 | 54.6% | D18S51 |
| VFD032 | 19 | GGGGCTGGCAATGCCCTGTT | B | Minus | 20 | 77531 | 77512 | 59.9 | 65.0% | |
| VFD033 | 20 | ACCCGACTACCAGCAACAACACA | A | Plus | 23 | 75612 | 75634 | 58.5 | 52.2% | |
| VFD034 | 21 | GGGGCTGGCAATGCCCTGTTT | B | Minus | 21 | 77531 | 77511 | 60.2 | 61.9% | |
| VFD035 | 22 | AGCCACTGCCTTGCCAACCA | A | Plus | 20 | 83732 | 83751 | 59.1 | 60.0% | PentaE |
| VFD036 | 23 | GTGGGGAGGCTGTGTAAGAAGTGT | B | Minus | 25 | 84996 | 84972 | 59.5 | 52.0% | |
| VFD037 | 24 | TCCCACCACTTTGCCCCAGGA | A | Plus | 21 | 83114 | 83134 | 59.7 | 61.9% | |
| VFD038 | 25 | TGGGGAGGCTGTGTAAGAAGTGT | B | Minus | 23 | 84994 | 84972 | 57.4 | 52.2% | |
| VFD043 | 26 | GGGAGAGGGAGAGGGTCTGGC | A | Plus | 21 | 80633 | 80653 | 59.4 | 71.4% | D5S818 |
| VFD044 | 27 | AGTGGGCCCTGGCCTGTGAT | B | Minus | 20 | 81642 | 81623 | 59.8 | 65.0% | |
| VFD047 | 28 | AGGCATGGCTGGGGAGTGAGT | A | Plus | 21 | 79513 | 79533 | 59.6 | 61.9% | |
| VFD048 | 29 | TCCCTTGGGCCTCAGCTTGC | B | Minus | 20 | 81445 | 81426 | 59.0 | 65.0% | |
| VFD051 | 30 | TGGGATGGGTTGCTGGACATGGT | A | Plus | 23 | 16706 | 16728 | 60.1 | 56.5% | D13S317 |
| VFD052 | 31 | AGCAAGGAATGCAGGCATGGTGT | B | Minus | 23 | 17758 | 17736 | 59.4 | 52.2% | |
| VFD057 | 32 | AAGGTCAGGCCTAGAAGTCTGCTT | A | Plus | 24 | 15285 | 15308 | 57.3 | 50.0% | |
| VFD058 | 33 | GGGTTGAGCCATAGGCAGCCC | B | Minus | 21 | 16933 | 16913 | 59.5 | 66.7% | |
| VFD059 | 34 | AGGCAATTTGCAGTTGGTGAAGCA | A | Plus | 24 | 103300 | 103323 | 58.3 | 45.8% | D7S820 |
| VFD060 | 35 | TGTCCCGTGAGGGTGTCAGGG | B | Minus | 21 | 105127 | 105107 | 59.8 | 66.7% | |
| VFD061 | 36 | GGCAATTTGCAGTTGGTGAAGCA | A | Plus | 23 | 103301 | 103323 | 57.3 | 47.8% | |
| VFD062 | 37 | GTCCCGTGAGGGTGTCAGGGA | B | Minus | 21 | 105126 | 105106 | 59.6 | 66.7% | |
| VFD065 | 38 | CCCTGCGGGAAGGAGAGGCT | A | Plus | 20 | 99873 | 99892 | 60.0 | 70.0% | D16S539 |
| VFD066 | 39 | GCAGGGTGCAGCTGGGGATG | B | Minus | 20 | 101636 | 101617 | 60.0 | 70.0% | |
| VFD067 | 40 | CTGCCGAGGTGCCTGACAGC | A | Plus | 20 | 100727 | 100746 | 60.0 | 70.0% | |
| VFD068 | 41 | TCCCAGTGGATGCCGGCTCA | B | Minus | 20 | 102618 | 102599 | 59.9 | 65.0% | |

| ID number | SEQ ID NO: | Sequence | PCR Ref. | Strand on template | length | Start | Stop | Tm (Primer Blast) | GC % | Loci |
|---|---|---|---|---|---|---|---|---|---|---|
| VFD081 | 42 | GTGGGCTGGAGGCCACGTTC | A | Plus | 20 | 37582 | 37601 | 60.0 | 70.0% | VWA |
| VFD082 | 43 | TCCAGGGCCCAACCCTAGCC | B | Minus | 20 | 39410 | 39391 | 59.9 | 70.0% | |

TABLE 1-continued

| | | | | | | | | | | |
|---|---|---|---|---|---|---|---|---|---|---|
| VFD085 | 44 | AGGCCACACCACCCCTCCTC | A | Plus | 20 | 37504 | 37523 | 59.8 | 70.0% | |
| VFD086 | 45 | CCAACCCTAGCCCCAGGGGG | B | Minus | 20 | 39402 | 39383 | 60.3 | 75.0% | |
| VFD087 | 46 | TGTGAGCAGCTAACGAGGCCT | A | Plus | 21 | 1398181 | 39838 | 57.9 | 57.1% | D8S1179 |
| VFD088 | 47 | GGGCTCCCGGGCTCACAGAA | B | Minus | 20 | 1417671 | 41748 | 60.5 | 70.0% | |
| VFD089 | 48 | AGACATCTGTGACCACACGGCCA | A | Plus | 23 | 1398451 | 39867 | 60.1 | 56.5% | |
| VFD090 | 49 | CAGGAAGGGGTGGGGCTCCC | B | Minus | 20 | 1417791 | 41760 | 60.5 | 75.0% | |
| VFD091 | 50 | CCGCGTTCAGAGCTGCCAGG | A | Plus | 20 | 62064 | 62083 | 60.4 | 70.0% | FGA |
| VFD092 | 51 | TCATGGAAGGCTGCAGGGCA | B | Minus | 20 | 63671 | 63652 | 58.3 | 60.0% | |
| VFD093 | 52 | GCCCAGCACTTCCGCGTTCA | A | Plus | 20 | 62053 | 62072 | 60.3 | 65.0% | |
| VFD094 | 53 | TCACTCTGGGCATGGACAGCGA | B | Minus | 22 | 64035 | 64014 | 59.9 | 59.1% | |
| VFD099 | 54 | CCTAGGCCAGAGGTGGCCCA | A | Plus | 20 | 42717 | 42736 | 59.6 | 70.0% | DYS19 |
| VFD100 | 55 | TGTGTGGAGACAGTAACGCCCT | B | Minus | 22 | 44085 | 44064 | 57.6 | 54.6% | |
| VFD101 | 56 | TCCCTGGTGCCATGGCTAGCA | A | Plus | 21 | 42501 | 42521 | 59.9 | 61.9% | |
| VFD102 | 57 | TGTGTGGAGACAGTAACGCCCTGA | B | Minus | 24 | 44085 | 44062 | 59.6 | 54.2% | |
| VFD105 | 58 | AGGCAGGAGGGTGCTGGAGC | A | Plus | 20 | 174327 | 174346 | 60.5 | 70.0% | AMELY |
| VFD106 | 59 | GCAGGCGCCAAACACTTGGC | B | Minus | 20 | 175386 | 175367 | 60.0 | 65.0% | (AC013412) |
| VFD107 | 60 | TGGTCAGGCAGGAGGGTGCT | A | Plus | 20 | 174322 | 174341 | 59.5 | 65.0% | |
| VFD108 | 61 | ACCCCGGGTGCAACCAGAGT | B | Minus | 20 | 175414 | 175395 | 60.0 | 65.0% | |
| VFD115 | 62 | CTCCTCCCTGGACCCCAGGC | A | Plus | 20 | 70992 | 71011 | 60.0 | 75.0% | AMELX |
| VFD116 | 63 | GGCTGCTGGGACGACACAGG | B | Minus | 20 | 72096 | 72077 | 59.7 | 70.0% | (AC002366) |
| VFD125 | 64 | CCACAGGCCAAGGGCTTCCG | A | Plus | 20 | 75866 | 75885 | 59.97 | 70.00% | TH01 |
| VFD126 | 65 | GCCGCACAGGGGACCCTTTC | B | Minus | 20 | 77299 | 77280 | 59.97 | 70.00% | |
| VFD128 | 66 | CTGGGCTGCCAGAAAGCCCC | A | Plus | 20 | 75485 | 75504 | 59.97 | 70.00% | |
| VFD129 | 67 | TGTGCCAGGGAGCCCAAGGT | B | Minus | 20 | 76693 | 76674 | 60.04 | 65.00% | |
| VFD140 | 68 | CTGCCACTGCCTGCACCCAA | A | Plus | 20 | 28416 | 28435 | 59.83 | 65.00% | CSF1PO |
| VFD141 | 69 | GCAACGTGCAGGGCAAGCAC | B | Minus | 20 | 29656 | 29637 | 59.98 | 65.00% | |
| VFD144 | 70 | TCAGCGTGGCGTTCAAGGCT | A | Plus | 20 | 27101 | 27120 | 59.28 | 60.00% | |
| VFD145 | 71 | GGGGAGCAGAGGAGGTGGCA | B | Minus | 20 | 28994 | 28975 | 59.89 | 70.00% | |

TABLE 2

| ID number | Loci | Amplicon size | STR nucleotide position | Position of repeat | Validated |
|---|---|---|---|---|---|
| VFD003 | TPOX | 1406 | 53,365-53,634 | End | X |
| VFD004 | | | | | |
| VFD138 | | 2532 | | Middle | X |
| VFD139 | | | | | |
| VFD009 | D3S1358 | 1228 | 77,721-77,851 | End | X |
| VFD010 | | | | | |
| VFD011 | | 1069 | | End | X |
| VFD012 | | | | | |
| VFD025 | D21S11 | 1566 | 4,267-4,489 | Middle | X |
| VFD026 | | | | | |
| VFD029 | | 1732 | | Middle | X |
| VFD030 | | | | | |
| VFD031 | D18S51 | 2117 | 75,615-75,944 | End | X |
| VFD032 | | | | | |
| VFD033 | | 1920 | | End | X |
| VFD034 | | | | | |
| VFD035 | PentaE | 1265 | 84,386-84,764 | End | X |
| VFD036 | | | | | |
| VFD037 | | 1881 | | End | X |
| VFD038 | | | | | |
| VFD043 | D5S818 | 1010 | 80,858-80,992 | End | X |
| VFD044 | | | | | |
| VFD047 | | 1933 | | Middle | X |
| VFD048 | | | | | |
| VFD051 | D13S317 | 1053 | 16,729-16,920 | End | X |
| VFD052 | | | | | |
| VFD057 | | 1649 | | End | X |
| VFD058 | | | | | |
| VFD059 | D7S820 | 1828 | 103,776-104,018 | End | X |
| VFD060 | | | | | |
| VFD061 | | 1826 | | End | X |
| VFD062 | | | | | |
| VFD065 | D16S539 | 1764 | 100,764-101,051 | Middle | X |
| VFD066 | | | | | |
| VFD067 | | 1892 | | End | X |
| VFD068 | | | | | |
| VFD081 | VWA | 1829 | 38,329-38,479 | Middle | X |
| VFD082 | | | | | |
| VFD085 | | 1899 | | Middle | X |
| VFD086 | | | | | |
| VFD087 | D8S1179 | 1950 | 140,044-140,270 | Middle | X |
| VFD088 | | | | | |
| VFD089 | | 1935 | | Middle | X |
| VFD090 | | | | | |
| VFD091 | FGA | 1608 | 63,318-63,663 | End | X |
| VFD092 | | | | | |
| VFD093 | | 1983 | | Middle | X |
| VFD094 | | | | | |
| VFD099 | DYS19 | 1369 | 43,180-43,431 | Middle | X |
| VFD100 | | | | | |
| VFD101 | | 1585 | | Middle | X |
| VFD102 | | | | | |
| VFD105 | AMELY | 1060 | 174,352-174,569 | End | X |
| VFD106 | (AC013412) | | | | |
| VFD107 | | 1093 | | End | X |
| VFD108 | | | | | |
| VFD115 | AMELX | 1105 | 71,868-72,079 | End | X |
| VFD116 | (AC002366) | | | | |

TABLE 2-continued

| ID number | Loci | Amplicon size | STR nucleotide position | Position of repeat | Validated |
|---|---|---|---|---|---|
| VFD125 VFD126 | TH01 | 1434 | 76,477-76,644 | Middle | ? |
| VFD128 VFD129 | | 1209 | | End | X |
| VFD140 VFD141 | CSF1PO | 1241 | 28,622-28,970 | Front | X |
| VFD144 VFD145 | | 1894 | | End | X |

TABLE 3

| Superset | FBI | UK | ESS | Additional European loci | Germany | ISSOL | Sinofiler |
|---|---|---|---|---|---|---|---|
| D1S1656 | | | D1S1656 | | | D1S1656 | |
| D2S1338 | | D2S1338 | | D2S1338 | | D2S1338 | D2S1338 |
| TPOX | TPOX | | | | | TPOX | TPOX |
| D2S441 | | | D2S441 | | | D2S441 | |
| D3S1358 | D3S1358 | D3S1358 | D3S1358 | | D3S1358 | D3S1358 | D3S1358 |
| FGA | FGA | FGA | FGA | | FGA | FGA | FGA |
| D5S818 | D5S818 | | | | | D5S818 | D5S818 |
| CSF1P0 | CSF1PO | | | | | CSF1P0 | CSF1P0 |
| SE33 | | | | SE33 | SE33 | SE33 | |
| D6S1043 | | | | | | | D6S1043 |
| D7S820 | D7S820 | | | | | D7S820 | D7S820 |
| D8S1179 | D8S1179 | D8S1179 | D8S1179 | | D8S1179 | D8S1179 | D8S1179 |
| D10S1248 | | | D10S1248 | | | D10S1248 | |
| TH01 | TH01 | TH01 | TH01 | | TH01 | TH01 | TH01 |
| vWA | vWA | vWA | vWA | | vWA | vWA | vWA |
| D12S391 | | | D12S391 | | | D12S391 | D12S391 |
| D13S317 | D13S317 | | | | | D13S317 | D13S317 |
| Penta E | | | | | | Penta E | |
| D16S539 | D16S539 | D16S539 | | D16S539 | | D16S539 | D16S539 |
| D18S51 | D18S51 | D18S51 | D18S51 | | D18S51 | D18S51 | D18S51 |
| D19S433 | | D19S433 | | D19S433 | | D19S433 | D19S433 |
| D21S11 | D21S11 | D21S11 | D21S11 | | D21S11 | D21S11 | D21S11 |
| Penta D | | | | | | Penta D | |
| D22S1045 | | | D22S1045 | | | D22S1045 | |

---

What is claimed is:

1. A method for identifying repeating sequences in a target nucleic acid comprising repeating sequences and non-repeating sequences, the method comprising the steps of
sequencing the target nucleic acid to obtain sequence data;
digitizing, with one or more processors, the sequence data;
applying, with the one or more processors, wavelet packet decomposition (WPD) to decompose the digitized sequence data into non-periodic signal data and periodic signal data comprising coefficients;
classifying, with the one or more processors, the non-periodic signal data into a non-repeat bin and the periodic signal data into a repeat bin based upon the coefficients; and
identifying the repeating sequences in the target nucleic acid by matching, with the one or more processors, only the coefficients from the periodic signal data in the repeat bin to reference coefficients generated from WPD of a reference sequence.

2. The method of claim 1 wherein the repeating sequences comprise different loci.

3. The method of claim 2 wherein different repeating sequence alleles at a locus have distinguishable coefficients and the distinguishable coefficients allow the different repeating sequence alleles to be distinguished from each other and from other short tandem repeat (STR) loci.

4. The method of claim 1 wherein the target nucleic acid comprises more than one allele for each of the repeating sequences in the target nucleic acid.

5. The method of claim 4 wherein the different alleles have distinguishable coefficients and wherein the distinguishable coefficients allow the different alleles to be distinguished from each other.

6. The method of claim 1 wherein the method provides information selected from the group consisting of the location, the frequency, and the length of the repeating sequences, or a combination thereof, in the target nucleic acid.

7. The method of claim 1 wherein one or more repeating sequences identified are compared to sequence data in a DNA database.

8. The method of claim 7 wherein the database is a national government DNA database.

9. The method of claim 8 wherein the database is selected from the group consisting of CODIS, NDNAD, and FNAEG.

10. The method of claim 9 wherein the database is CODIS.

11. The method of claim 9 wherein the database is NDNAD.

12. The method of claim 7 wherein the database is GenBank, EMBL, DDBJ or a similar government database, or a custom sequence database.

13. The method of claim 7 wherein the repeating sequences are short tandem repeats (STRs) and the sequence data in the DNA database comprises short tandem repeat (STR) loci.

14. The method of claim 7 wherein the repeating sequences are short tandem repeats (STRs) and the sequence data in the DNA database comprises about 7 to about 16 short tandem repeat (STR) loci.

15. The method of claim 1 wherein the reference sequence comprises short tandem repeats (STRs).

16. The method of claim 15 wherein the reference sequence further comprises an allele for each short tandem repeat (STR).

17. The method of claim 1 wherein the target nucleic acid is a DNA or RNA.

18. The method of claim 1 wherein the repeating sequences are tandem repeats.

19. The method of claim 1 wherein applying WPD comprises recursively applying, with the one or more processors, low-pass and high-pass quadrature mirror filters to the digitized sequence data.

20. The method of claim 1 wherein classifying the non-periodic signal data into a non-repeat bin and the periodic signal data into a repeat bin based upon the coefficients comprises determining whether particular data is the non-periodic signal data or periodic signal data by comparing, with the one or more processors, a maximum coefficient from among the coefficients to a threshold value.

* * * * *

SEQUENCE LISTING

<160> NUMBER OF SEQ ID NOS: 72

<210> SEQ ID NO 1
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
atctatctat ctatctatct atct                                          24

<210> SEQ ID NO 2
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tctatctgtc tatctatcta tctatctatc tatctatcta tctatctatc tatcta       56

<210> SEQ ID NO 3

```
<211> LENGTH: 115
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
tctatctatc tatctatctg tctgtctgtc tgtctgtctg tctatctatc tatatctatc      60
tatctatcat ctatctatcc atatctatct atctatctat ctatctatct atcta           115

<210> SEQ ID NO 4
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tctatctgtc tgtctgtcta tctatctatc tatctatcta tctatctatc tatctatcta      60

<210> SEQ ID NO 5
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cactgaatga atgaatgaat gaatgaatgt ttgg                                  34

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tgtcgcgact ccccctgtgt                                                  20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
ggcccgatcc cctgacacct                                                  20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 8
gggccatccc agccctctca                                                  20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tggctgggac cccctttgct                                                  20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tgccgaggca cagaagcgtg                                                  20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
tgccagggca ctgctccaga                                                  20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
gccagaccat ggctgctggg                                                  20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tgcccacttc tgcccaggga                                                  20

<210> SEQ ID NO 14
<211> LENGTH: 22
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
gggcatgaat gagggcatgg ct                                              22

<210> SEQ ID NO 15
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
catgccattt atggggcaac aggt                                            24

<210> SEQ ID NO 16
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
gagggcatga atgagggcat gg                                              22

<210> SEQ ID NO 17
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
acagctcact ccaaggacag ctgt                                            24

<210> SEQ ID NO 18
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
agccgacaaa aggctatggg ct                                              22

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ggggctggca atgccctgtt                                                 20
```

<210> SEQ ID NO 20
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
acccgactac cagcaacaac aca                                          23

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggggctggca atgccctgtt t                                            21

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
agccactgcc ttgccaacca                                              20

<210> SEQ ID NO 23
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
tgtggggagg ctgtgtaaga agtgt                                        25

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
tcccaccact ttgccccagg a                                            21

<210> SEQ ID NO 25
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

```
                              Synthetic primer"

<400> SEQUENCE: 25
tggggaggct gtgtaagaag tgt                                              23

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
gggagaggga gagggtctgg c                                                21

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
agtgggccct ggcctgtgat                                                  20

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
aggcatggct ggggagtgag t                                                21

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
tcccttgggc ctcagcttgc                                                  20

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tgggatgggt tgctggacat ggt                                              23

<210> SEQ ID NO 31
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
agcaaggaat gcaggcatgg tgt                                        23

<210> SEQ ID NO 32
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
aaggtcaggc ctagaagtct gctt                                       24

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gggttgagcc ataggcagcc c                                          21

<210> SEQ ID NO 34
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
aggcaatttg cagttggtga agca                                       24

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
tgtcccgtga gggtgtcagg g                                          21

<210> SEQ ID NO 36
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
```

```
ggcaatttgc agttggtgaa gca                                         23
```

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37

```
gtcccgtgag ggtgtcaggg a                                           21
```

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38

```
ccctgcggga aggagaggct                                             20
```

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39

```
gcagggtgca gctggggatg                                             20
```

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40

```
ctgccgaggt gcctgacagc                                             20
```

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41

```
tcccagtgga tgccggctca                                             20
```

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
gtgggctgga ggccacgttc                                               20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tccagggccc aaccctagcc                                               20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
aggccacacc acccctcctc                                               20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
ccaaccctag ccccaggggg                                               20

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
tgtgagcagc taacgaggcc t                                             21

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gggctcccgg gctcacagaa                                               20

<210> SEQ ID NO 48

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
agacatctgt gaccacacgg cca                                           23

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
caggaagggg tggggctccc                                               20

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
ccgcgttcag agctgccagg                                               20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tcatggaagg ctgcagggca                                               20

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
gcccagcact tccgcgttca                                               20

<210> SEQ ID NO 53
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
```
tcactctggg catggacagc ga                                              22

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
cctaggccag aggtggccca                                                 20

<210> SEQ ID NO 55
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
tgtgtggaga cagtaacgcc ct                                              22

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tccctggtgc catggctagc a                                               21

<210> SEQ ID NO 57
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
tgtgtggaga cagtaacgcc ctga                                            24

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
aggcaggagg gtgctggagc                                                 20

<210> SEQ ID NO 59
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 59
gcaggcgcca aacacttggc                                                   20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
tggtcaggca ggagggtgct                                                   20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
accccgggtg caaccagagt                                                   20

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
ctcctccctg gaccccaggc                                                   20

<210> SEQ ID NO 63
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ggctgctggg acgacacagg                                                   20

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
ccacaggcca agggcttccg                                                   20
```

```
<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
gccgcacagg ggacccttc                                              20

<210> SEQ ID NO 66
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
ctgggctgcc agaaagcccc                                             20

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
tgtgccaggg agcccaaggt                                             20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
ctgccactgc ctgcacccaa                                             20

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
gcaacgtgca gggcaagcac                                             20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 70
tcagcgtggc gttcaaggct                                              20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
ggggagcaga ggaggtggca                                              20

<210> SEQ ID NO 72
<211> LENGTH: 151
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
cctttggggg catctcttat actcatgaaa tcaacagagg cttgcatgta tctatctgtc   60
tgtctatcta tctatctatc tatctatcta tctatctatc tatgagacag ggtcttgctc  120
tgtcacccag attggactgc agtgggggaa t                                 151
```